United States Patent

Taniguchi et al.

[11] Patent Number: 6,005,111
[45] Date of Patent: Dec. 21, 1999

[54] COLOR DEVELOPING AGENT, PROCESSING COMPOSITION AND COLOR IMAGE-FORMING METHOD

[75] Inventors: Masato Taniguchi; Kiyoshi Morimoto; Keizo Kimura; Kazumi Nii; Shigeo Hirano, all of Minami-Ashigara, Japan

[73] Assignee: Fuji Photo Film Co., Ltd., Minami-Ashigara, Japan

[21] Appl. No.: 09/016,272

[22] Filed: Jan. 30, 1998

Related U.S. Application Data

[62] Division of application No. 08/893,189, Jul. 15, 1997, which is a continuation of application No. 08/787,325, Jan. 28, 1997, abandoned, which is a continuation of application No. 08/393,538, Feb. 23, 1995, abandoned.

[30] Foreign Application Priority Data

Feb. 25, 1994 [JP] Japan .................................. 6-028529

[51] Int. Cl.$^6$ .......................... A47C 1/12; C07D 215/02; C07D 215/38
[52] U.S. Cl. ........................ 546/166; 430/448; 546/171
[58] Field of Search ................... 546/166, 171

[56] References Cited

U.S. PATENT DOCUMENTS

| | | | |
|---|---|---|---|
| 2,196,739 | 4/1940 | Peterson | 430/470 |
| 2,387,751 | 10/1945 | Dickey et al. | 546/156 |
| 2,566,259 | 8/1951 | Thirtle et al. | 430/476 |

FOREIGN PATENT DOCUMENTS

| | | |
|---|---|---|
| 069585 | 1/1983 | European Pat. Off. . |
| A3524519 | 1/1986 | Germany . |
| 4-45440 | 2/1992 | Japan . |

OTHER PUBLICATIONS

CA 117:181647, abstract of JP 04045440A2, published Feb. 14, 1992.
CA 105:210421, abstract of DE 3524519, published Jan. 16, 1986.
CA 119:282073, abstract of JP 04371948, published Dec. 24, 1992.

*Primary Examiner*—D. Margaret M. Mach
*Attorney, Agent, or Firm*—Burns, Doane, Swecker & Mathis, LLP

[57] ABSTRACT

A method for forming a color image comprises the step of developing an image-wise exposed silver halide color photographic photosensitive material at the presence of a 6-aminotetrahydroquinoline color developing agent which is the following compound or its analoge. According to this method, the rapid process can be attained and an image of a low fog density can be obtained.

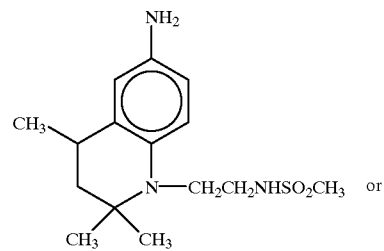

or

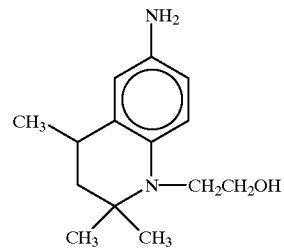

5 Claims, No Drawings

COLOR DEVELOPING AGENT, PROCESSING COMPOSITION AND COLOR IMAGE-FORMING METHOD

This application is a divisional of application Ser. No. 08/893,189, filed Jul. 15, 1997, which is a continuation of application Ser. No. 08/787,325, filed Jan. 28, 1997 now abandoned, which is a continuation of application Ser. No. 08/393,538, filed Feb. 23, 1995 now abandoned.

BACKGROUND OF THE INVENTION

The present invention relates to a new developing agent for silver halide color photographs, a processing composition containing the developing agent, and a method for forming a color image with the processing solution. In particular, the present invention relates to a developing agent for color photographs suitable for rapid processing of color photographs and capable of forming an image with only a slight fog, a processing composition containing the developing agent, and a method for forming a color image with the processing solution.

As mini-labs for processing photosensitive materials within the shops and the amount of color negative films used in the field of news photos are increasing recently, the demand for completion of the development process in a shorter time to immediately provide the prints to the customers or to immediately place the photo in newspapers or the like is rapidly increasing. The demand for reduction of the processing time is becoming more and more eager in processing color negative films, since the time necessitated therefor is longer than that necessitated for processing color papers.

For the reduction of the time necessitated for the color development step in the processing steps, Japanese Patent Unexamined Published Application (hereinafter referred to as "J. P. KOKAI") No. Hei 4-45440 discloses a method wherein tetrahydroquinoline or a dihydroindole derivative is used as the color developing agent. The use of such a compound as the color developing gent is also described in U.S. Pat. Nos. 2,196,739 and 2,566,259. In particular, it is described in J. P. KOKAI No. Hei 4-45440 that the time of the color developing step can be reduced by using such a compound as the color developing agent even in color photograhic photosensitive materials mainly comprising a silver bromoiodide emulsion such as color negative films.

However, when the color photographic photosensitive material mainly comprising the silver bromoiodide emulsion is developed with one of the compounds disclosed in the above-described specifications, there are some disadvantages in that the density of the formed image in the unexposed area is high, in other words, the fog is serious.

SUMMARY OF THE INVENTION

An object of the invention is to provide a method for forming a color image which makes it possible to rapidly process an image-wise exposed silver halide color photographic photosensitive material and to obtain a color image having a low fog density.

Another object of the invention is to provide a color developing agent suitable for use in the rapid processing method and capable of realizing only a low fog density.

Another object of the invention is to provide a composition containing the developing agent for processing a silver halide color photographic photosensitive material.

These and other objects of the present invention will be apparent from the following description and Examples.

The above-described objects have been attained with specific 6-aminotetrahydroquinoline color developing agent.

The first aspect of the present invention, there is provided a method for forming a color image which comprises the step of developing an image-wise exposed a silver halide color photographic photosensitive material at the presence of a 6-aminotetrahydroquinoline color developing agent represented by the following formula (I).

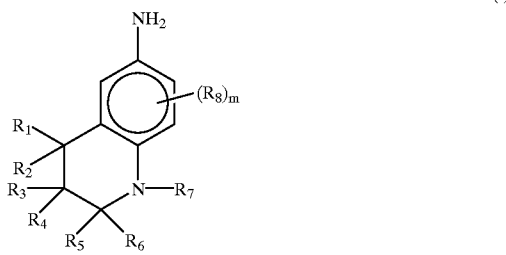

wherein $R_1$, $R_2$, $R_3$, $R_4$, $R_5$ and $R_6$ may be the same or different from one another and they each represent a hydrogen atom or substituent, with the proviso that in at least one of the groups of $R_1$ and $R_2$, $R_3$ and $R_4$, and $R_5$ and $R_6$, both of them are the substituents, $R_7$ represents an alkyl, aryl or heterocyclic group, $R_8$ represents a substituent, and m represents an integer of 0 to 3.

The second aspect of the present invention, there is provided the 6-aminotetrahydroquinoline color developing agent.

The third aspect of the present invention, there is provided a processing composition for silver halide color photographic materials which comprises the 6-aminotetrahydroquinoline color developing agent.

Although the color developing agents of the present invention are included in the claim of the above-described U.S. Pat. No. 2,196,739, the specification of this patent has no specific description on the compounds corresponding to the color developing agents of the present invention and there is given no direct description or indirect description suggesting the possibility of reducing the time necessitated for the color developing step and reducing the fog density at the same time, which is the object of the present invention.

The tetrahydroquinoline color developing agent of the present invention is characterized in that at least one of the three carbon atoms forming the saturated ring of tetrahydroquinoline is substituted with two substituents, in other words, it has no hydrogen atom in this respect. The effect of the present invention cannot be obtained without such a structure, and therefore it is impossible to expect this fact from the specification of the above-described U.S. Pat. No. 2,196,739.

DESCRIPTION OF THE PREFERRED EMBODIMENTS OF THE INVENTION

The detailed description will be made on $R_1$, $R_2$, $R_3$, $R_4$, $R_5$, $R_6$, $R_7$, $R_8$ and m in the compounds represented by the above-mentioned general formula (I) in the present invention.

$R_1$, $R_2$, $R_3$ and $R_4$ may be the same or different from one another and they each represent a hydrogen atom or substituent. In particular, $R_1$, $R_2$, $R_3$ and $R_4$ are each a hydrogen atom or substituent. Examples of the substituents include halogen atoms, and alkyl, aryl, heterocyclic, cyano, nitro, hydroxyl, carboxyl, sulfo, alkoxy, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic-oxy, azo, acyloxy, carbamoyloxy, silyl, silyloxy, aryloxycarbonylamino, imido, heterocyclic thio, sulfinyl, phosphonyl, aryloxycarbonyl and acyl groups. They may be substituted with an alkyl, alkenyl, alkynyl, aryl, hydroxyl, nitro or cyano group, a halogen atom or other substituent containing an oxygen, nitrogen, sulfur or carbon atom.

Furthermore, the detailed description will be made on examples of the substituents $R_1$, $R_2$, $R_3$ and $R_4$. The halogen atoms are, for example, fluorine and chlorine atoms. Examples of the alkyl groups are linear, branched or cyclic alkyl groups having 1 to 16 carbon atoms, preferably 1 to 6 carbon atoms, such as methyl, ethyl, propyl, isopropyl, t-butyl, 2-hydroxyethyl, 3-hydroxypropyl, benzyl, 2-methanesulfonamidoethyl, 3-methanesulfonamidopropyl, 2-methanesulfonylethyl, 2-methoxyethyl, cyclopentyl, 2-acetamidoethyl, hydroxymethyl, 2-carboxyethyl, 2-carbamoylethyl, 3-carbamoylpropyl, 2,3-dihydroxypropyl, 3,4-dihydroxybutyl, methanesulfonamidomethyl, n-hexyl, 2-hydroxypropyl, 4-hydroxybutyl, 2-carbamoylaminoethyl, 3-carbamoylaminopropyl, 4-carbamoylaminobutyl, 4-carbamoylbutyl, 2-carbamoyl-1-methylethyl, carbamoylaminomethyl and 4-nitrobutyl groups.

The aryl groups are those having 6 to 24 carbon atoms such as phenyl, naphthyl and p-methoxyphenyl groups. The heterocyclic groups are five-membered or six-membered, saturated or unsaturated heterocyclic groups having 1 to 5 carbon atoms and one or more oxygen, nitrogen and sulfur atoms. The number of the hetero-atoms and kind of the elements constituting the ring may be one or more. Examples of the heterocyclic groups include 2-furyl, 2-thienyl, 2-pyrimidinyl, 2-benzotriazolyl, imidazolyl and pyrazolyl groups.

The alkoxy groups are those having 1 to 16 carbon atoms, preferably 1 to 6 carbon atoms, such as methoxy, ethoxy, 2-methoxyethoxy and 2-methanesulfonylethoxy groups. The aryloxy groups are those having 6 to 24 carbon atoms such as phenoxy, p-methoxyphenoxy, m-(3-hydroxypropionamido)phenoxy groups. The acylamino groups are those having 1 to 16 carbon atoms, preferably 1 to 6 carbon atoms, such as acetamido, 2-methoxypropionamido and p-nitrobenzoylamido groups.

The alkylamino groups are those having 1 to 16 carbon atoms, preferably 1 to 6 carbon atoms, such as dimethylamino, diethylamino and 2-hydroxyethylamino groups. The anilino groups are those having 6 to 24 carbon atoms such as anilino, m-nitroanilino and N-methylanilino groups. The ureido groups are those having 1 to 16 carbon atoms, preferably 1 to 6 carbon atoms, such as ureido, methylureido, N,N-diethylureido and 2-methanesulfonamidoethylureido groups.

The sulfamoylamino groups are those having 0 to 16 carbon atoms, preferably 0 to 6 carbon atoms such as dimethylsulfamoylamino, methylsulfamoylamino and 2-methoxyethylsulfamoylamino groups. The alkylthio groups are those having 1 to 16 carbon atoms, preferably 1 to 6 carbon atoms, such as methylthio, ethylthio and 2-phenoxyethylthio groups. The arylthio groups are those having 6 to 24 carbon atoms such as phenylthio, 2-carboxyphenylthio and 4-cyanophenylthio groups. The alkoxycarbonylamino groups are those having 2 to 16 carbon atoms, preferably 2 to 6 carbon atoms such as methoxycarbonylamino, ethoxycarbonylamino and 3-methanesulfonylpropoxycarbonylamino groups.

The sulfonamido groups are those having 1 to 16 carbon atoms, preferably 1 to 6 carbon atoms, such as methanesulfonamido, p-toluenesulfonamido and 2-methoxyethanesulfonamido groups. The carbamoyl groups are those having 1 to 16 carbon atoms, preferably 1 to 6 carbon atoms, such as carbamoyl, N,N-dimethylcarbamoyl and N-ethylcarbamoyl groups. The sulfamoyl groups are those having 0 to 16 carbon atoms, preferably 0 to 6 carbon atoms, such as sulfamoyl, dimethylsulfamoyl and ethylsulfamoyl groups.

The sulfonyl groups are aliphatic or aromatic sulfonyl groups having 1 to 16 carbon atoms, preferably 1 to 6 carbon atoms, such as methanesulfonyl, ethanesulfonyl and 2-chloroethanesulfonyl groups. The alkoxycarbonyl groups are those having 1 to 16 carbon atoms, preferably 1 to 6 carbon atoms such as methoxycarbonyl, ethoxycarbonyl and t-butoxycarbonyl groups. The heterocyclic oxy groups are five-membered or six-membered, saturated or unsaturated heterocyclic oxy groups having 1 to 5 carbon atoms and at least one of oxygen, nitrogen and sulfur atoms. The number of the hetero atom constituting the ring and the kind of the element constituting it may be one or more. They include, for example, 1-phenyltetrazolyl-5-oxy, 2-tetrahydropyranyloxy and 2-pyridyloxy groups.

The azo groups are those having 1 to 16 carbon atoms, preferably 1 to 6 carbon atoms, such as phenylazo, 2-hydroxy-4-propanoylphenylazo and 4-sulfophenylazo groups. The acyloxy groups are those having 1 to 16 carbon atoms, preferably 1 to 6 carbon atoms, such as acetoxy, benzoyloxy and 4-hydroxybutanoyloxy groups. The carbamoyloxy groups are those having 1 to 16 carbon atoms, preferably 1 to 6 carbon atoms, such as N,N-dimethylcarbamoyloxy, N-methylcarbamoyloxy and N-phenylcarbamoyloxy groups.

The silyl groups are those having 3 to 16 carbon atoms, preferably 3 to 6 carbon atoms, such as trimethylsilyl, isopropyldiethylsilyl and t-butyldimethylsilyl groups. The silyloxy groups are those having 3 to 16 carbon atoms, preferably 3 to 6 carbon atoms, such as trimethylsilyloxy, triethylsilyloxy and diisopropylethylsilyloxy groups. The aryloxycarbonylamino groups are those having 7 to 24 carbon atoms such as phenoxycarbonylamino, 4-cyanophenoxycarbonylamino and 2,6-dimethoxyphenoxycarbonylamino groups.

The imido groups are those having 4 to 16 carbon atoms such as N-succinimido and N-phthalimido groups. The heterocyclic thio groups are five-membered or six-membered, saturated or unsaturated heterocyclic thio groups having 1 to 5 carbon atoms and at least one of oxygen, nitrogen and sulfur atoms. The number of the hetero-atoms constituting the ring and the kind of the element constituting it may be one or more. They include, for example, 2-benzothiazolylthio and 2-pyridylthio groups.

The sulfinyl groups are those having 1 to 16 carbon atoms, preferably 1 to 6 carbon atoms, such as methanesulfinyl, benzenesulfinyl and ethanesulfinyl groups. The phosphonyl groups are those having 2 to 16 carbon atoms, preferably 2 to 6 carbon atoms, such as methoxyphosphonyl, ethoxyphosphonyl and phenoxyphosphonyl groups. The aryloxycarbonyl groups are those having 7 to 24 carbon atoms such as henoxycarbonyl, 2-methylphenoxycarbonyl and 4-acetamidophenoxycarbonyl groups. The acyl groups are those having 1 to 16 carbon atoms, preferably 1 to 6 carbon atoms, such as acetyl, benzoyl and 4-chlorobenzoyl groups.

$R_5$ and $R_6$ each represent a hydrogen atom or substituent which is an alkyl, aryl or heterocyclic group. The details of $R_5$ and $R_6$ are the same as those described above with reference of $R_1$, $R_2$, $R_3$ and $R_4$, with the proviso that when $R_5$ and $R_6$ are each a heterocyclic group, it is bonded through a carbon atom constituting the hetero ring of the heterocyclic group.

$R_7$ represents an alkyl, aryl or heterocyclic group. The details of $R_7$ is the same as those described above with reference of $R_1$, $R_2$, $R_3$ and $R_4$, with the proviso that when $R_7$ is an alkyl group, other group than a hydrogen atom and a carbon atom is not bonded to the carbon atom directly bonded to the nitrogen atom in the general formula (I) and that when $R_7$ is a heterocyclic group, it is bonded to the nitrogen atom in the general formula (I) through a carbon atom constituting the hetero-ring of the heterocyclic group. $R_8$ represents a substituent. The details of $R_8$ is the same as those described above with reference of $R_1$, $R_2$, $R_3$ and $R_4$. m represents an integer of 0 to 3.

Among the compounds of the general formula (I), particularly preferred are those of the following formula (II):

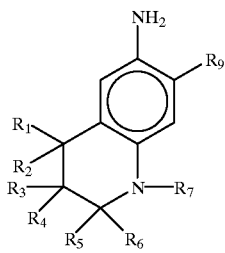

(II)

wherein $R_1$, $R_2$, $R_3$, $R_4$, $R_5$ and $R_6$ may be the same or different from one another and each represent a hydrogen atom or substituent, with the proviso that in at least one of the combinations of $R_1$ and $R_2$, $R_3$ and $R_4$, and $R_5$ and $R_6$, both of them are the substituents, $R_7$ represents an alkyl, aryl or heterocyclic group, and $R_9$ represents a hydrogen atom or substituent.

The description will be made on preferred combinations of $R_1$, $R_2$, $R_3$, $R_4$, $R_5$, $R_6$, $R_7$ and $R_9$ in the formula (II).

$R_9$ is a hydrogen atom, alkyl group or alkoxy group. $R_7$ is an alkyl group, and in the above-described combinations, it is preferred that $R_1$, $R_2$, $R_3$, $R_4$, $R_5$ and $R_6$ are each a hydrogen atom or an alkyl group. The alkyl and alkoxy groups herein include those substituted with other substituent.

In these combinations, it is preferred that at least one of $R_1$, $R_2$, $R_3$, $R_4$, $R_5$, $R_6$, $R_7$ and $R_9$ is an alkyl group substituted with a water-soluble group. More preferably, the alkyl group is that substituted with a hydroxyl, carboxyl, sulfo, alkoxy, acylamino, amino, alkylamino, ureido, sulfamoylamino, sulfonamido, carbamoyl, sulfamoyl or sulfonyl group. Particularly preferred is an alkyl group substituted with a hydroxyl, carboxyl, ureido or sulfonamido group.

In a more preferred combination, $R_9$ is a hydrogen atom, alkyl group having 1 to 6 carbon atoms or alkoxy group having 1 to 6 carbon atoms, $R_7$ is an alkyl group having 1 to 6 carbon atoms, and $R_1$, $R_2$, $R_3$, $R_4$, $R_5$ and $R_6$ each represent a hydrogen atom or an alkyl group having 1 to 3 carbon atoms.

In these combinations, it is preferred that at least one of $R_1$, $R_2$, $R_3$, $R_4$, $R_5$, $R_6$, $R_7$ and $R_9$ is an alkyl group substituted with a water-soluble group. More preferably, the alkyl group is that substituted with a hydroxyl, carboxyl, sulfo, alkoxy, acylamino, amino, alkylamino, ureido, sulfamoylamino, sulfonamido, carbamoyl, sulfamoyl or sulfonyl group. Particularly preferred is an alkyl group substituted with a hydroxyl, carboxyl, ureido or sulfonamido group.

In a still more preferred combination, $R_9$ is an alkyl group having 1 to 6 carbon atoms, $R_7$ is an alkyl group having 1 to 6 carbon atoms, and $R_1$, $R_2$, $R_3$, $R_4$, $R_5$ and $R_6$ each represent a hydrogen atom or an alkyl group having 1 to 3 carbon atoms.

In these combinations, it is preferred that at least one of $R_1$, $R_2$, $R_3$, $R_4$, $R_5$, $R_6$, $R_7$ and $R_9$ is an alkyl group substituted with a water-soluble group. More preferably, the alkyl group is that substituted with a hydroxyl, carboxyl, sulfo, alkoxy, acylamino, amino, alkylamino, ureido, sulfamoylamino, sulfonamido, carbamoyl, sulfamoyl or sulfonyl group. Particularly preferred is an alkyl group substituted with a hydroxyl, carboxyl, ureido or sulfonamido group.

In a further preferred combination, $R_9$ is a methyl group, $R_7$ is an alkyl group having 1 to 6 carbon atoms, and $R_1$, $R_2$, $R_3$, $R_4$, $R_5$ and $R_6$ each represent a hydrogen atom or an alkyl group having 1 to 3 carbon atoms.

In these combinations, it is preferred that at least one of $R_1$, $R_2$, $R_3$, $R_4$, $R_5$, $R_6$ and $R_7$ is an alkyl group substituted with a water-soluble group. More preferably, the alkyl group is that substituted with a hydroxyl, carboxyl, sulfo, alkoxy, acylamino, amino, alkylamino, ureido, sulfamoylamino, sulfonamido, carbamoyl, sulfamoyl or sulfcnyl group. Particularly preferred is an alkyl group substituted with a hydroxyl, carboxyl, ureido or sulfonamido group.

Examples of typical developing agents of the above general formula (I) will be given below, which by no means limit the present invention.

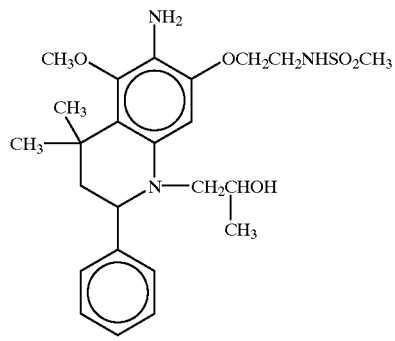

(D-1)

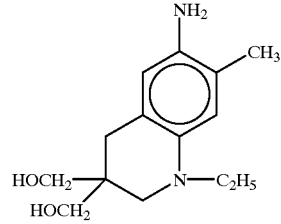

(D-2)

-continued
(D-3) 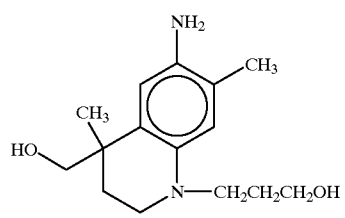
(D-4) 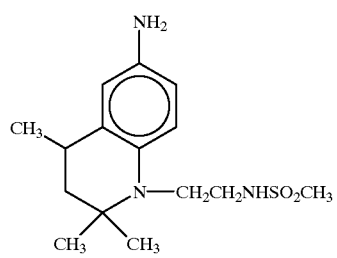
(D-5) 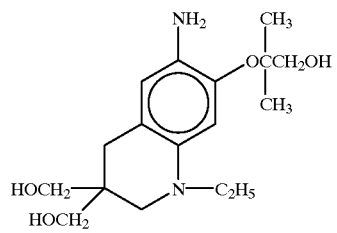
(D-6) 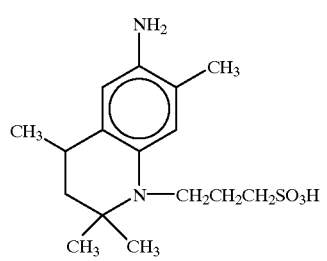
(D-7) 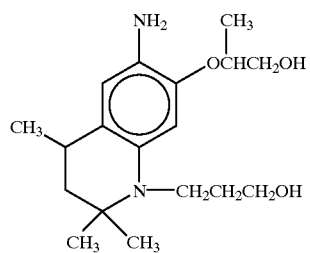
(D-8) 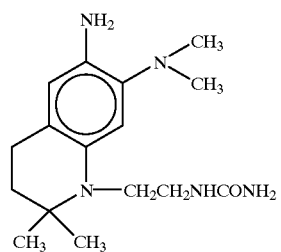
-continued
(D-9) 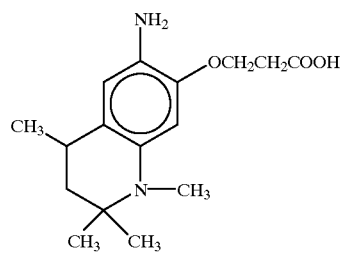
(D-10) 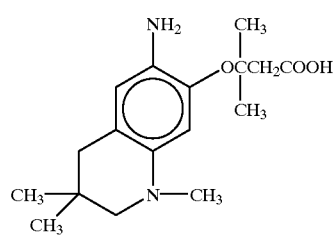
(D-11) 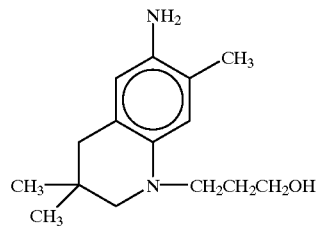
(D-12) 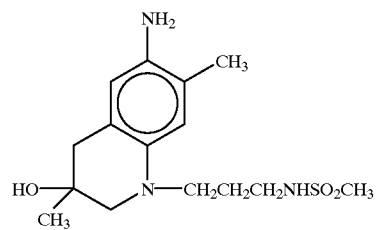
(D-13) 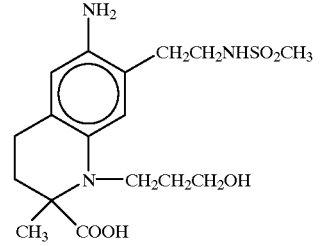
(D-14) 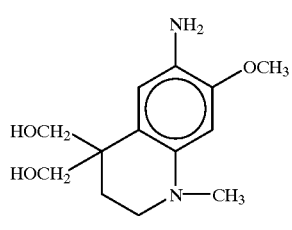

-continued
(D-15)
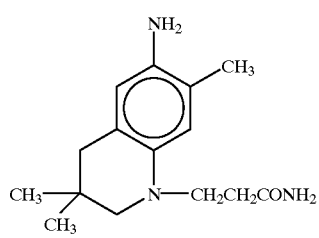
(D-16)
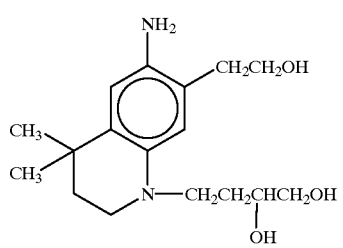
(D-17)
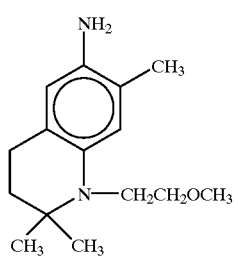
(D-18)
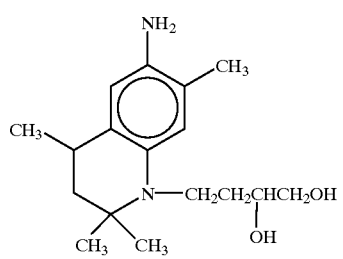
(D-19)
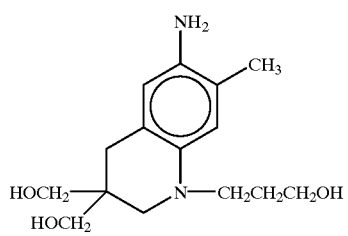
(D-20)
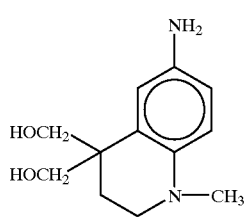
-continued
(D-21)
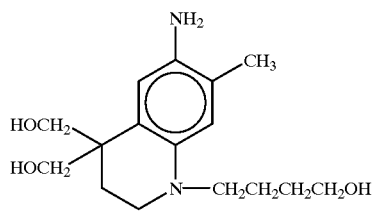
(D-22)
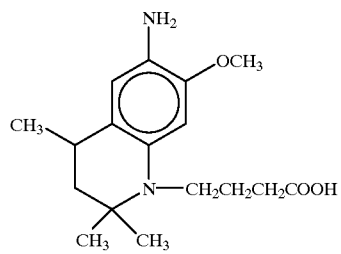
(D-23)
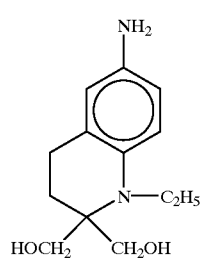
(D-24)
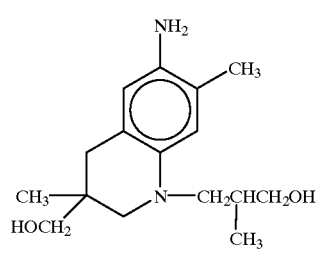
(D-25)
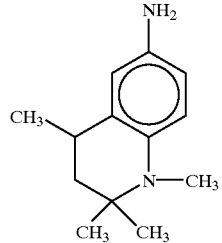
(D-26)
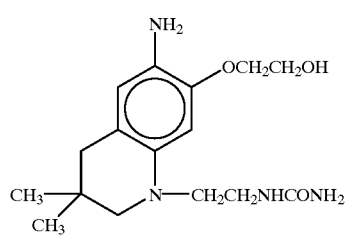

(D-27)
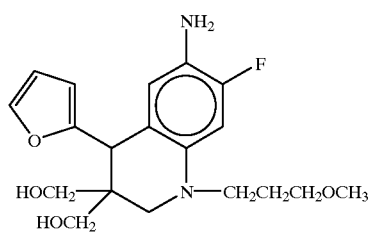
(D-28)
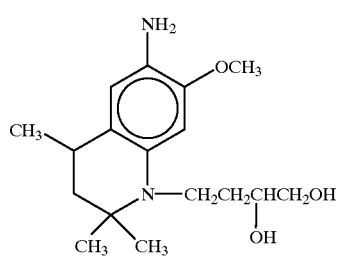
(D-29)
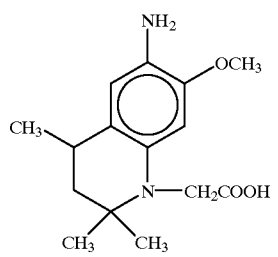
(D-30)
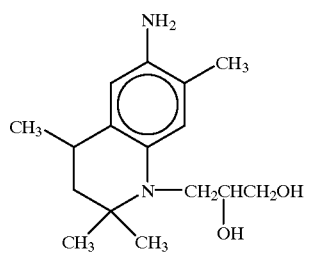
(D-31)
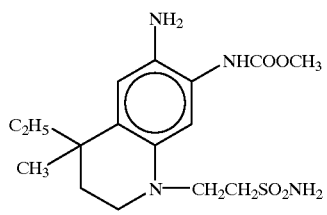
(D-32)
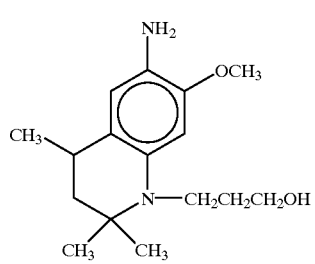
(D-33)
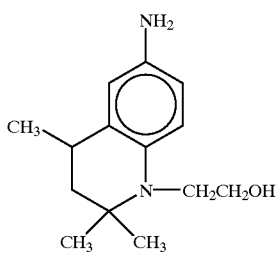
(D-34)
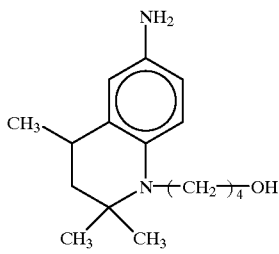
(D-35)
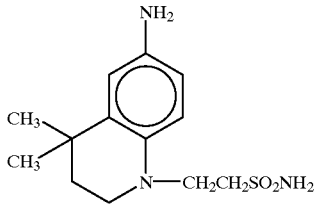
(D-36)
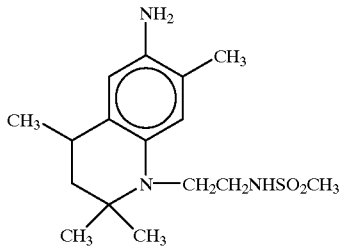
(D-37)
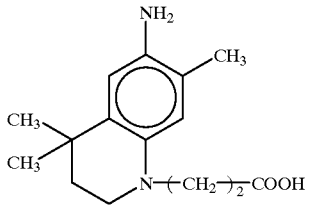
(D-38)
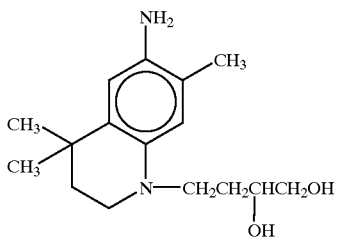

-continued

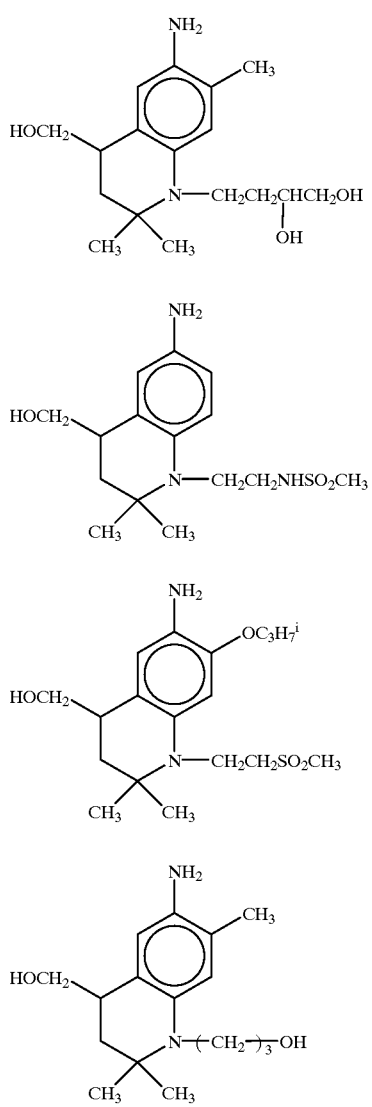

(D-39)

(D-40)

(D-41)

(D-42)

Since the compounds of the general formula (I) are very unstable when they are stored in the form of the free amines, they are usually stored in the form of salts with an inorganic or organic acid, and converted into the free amines when they are to be added to the processing solution. Examples of the inorganic and organic scids usable for converting the compounds of the general formula (I) into their salts include hydrochloric acid, sulfuric acid, phosphoric acid, p-toluenesulfonic acid, methanesulfonic acid and naphthalene-1,5-disulfonic acid. Among them, the sulfates and p-toluenesulfonates are preferred, and particularly the sulfates are most preferred.

The color developing agent of the present invention can be easily synthesized by, for example, a method described in Journal of the American Chemical Society, Vol. 73, p. 3100 (1951). Further, a method given in the following Synthesis Examples or the like can also be employed.

SYNTHESIS EXAMPLE 1

Compound (D-30) of the present invention as mentioned above was synthesized according to the following scheme:

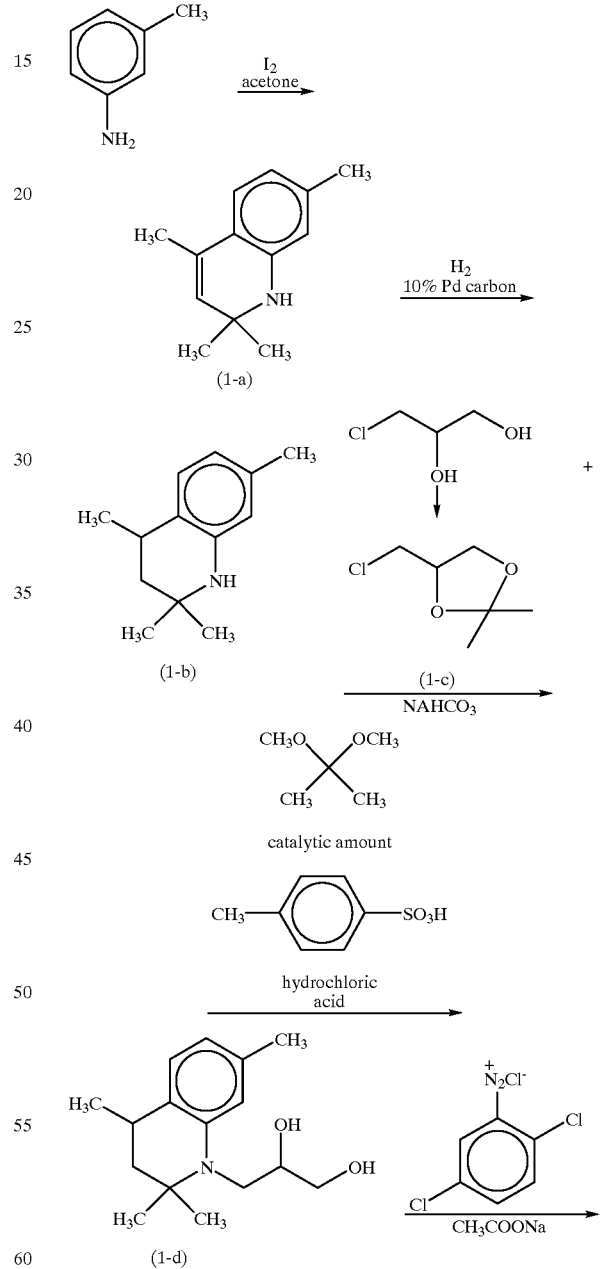

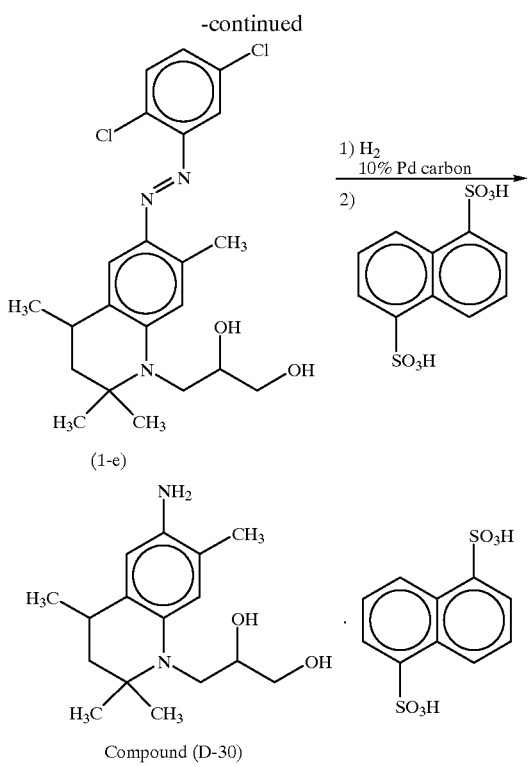

Compound (D-30)

Synthesis of Compound (1-a)

78.0 g of compound (1-a) was obtained from 214 g of m-toluidine by a method described in Organic Syntheses Collective Volume, Vol. III, p. 328.

Synthesis of Compound (1-b)

250 ml of ethanol was added to 69.6 g of (1-a) to obtain a solution. 0.55 g of 10% palladium carbons was added to the solution. The resultant mixture was brought into contact with hydrogen in an autoclave for 5 hours. The catalyst was filtered out by using Celite as a filter aid. The filtrate was concentrated to obtain 69.1 g of compound (1-b).

Synthesis of Compound (1-c)

680 ml of acetone and 2.2 g of p-toluenesulfonic acid monohydrate were added to 498 ml of 3-chloro-1,2-propanediol, and the resultant mixture was left to stand at room temperature for 15 hours. The mixture was then concentrated. Ethyl acetate was added to the residue. After washing with an aqueous solution of 2.0 g of sodium hydrogencarbonate and then with saturated common salt solution, the product was dried over Glauber's salt and concentrated to obtain 244 g of compound (1-c).

Synthesis of Compound (1-d)

150 ml of N,N-dimethyl acetamide, 292 g of (1-c), 34.2 g of sodium hydrogencarbonate and 61.1 g of sodium iodide were added to 73.5 g of compound (1-b), and the resultant mixture was stirred at 150° C. for 24 hours. Water was poured into the mixture. The product was extracted with ethyl acetate, washed with saturated aqueous common salt solution, dried over Glauber's salt and concentrated. 388 ml of water and 71 ml of 12 N hydrochloric acid were added to the product. The resultant mixture was stirred at room temperature for 5 hours. 84 g of sodium hydrogencarbonate was added thereto. The product was extracted with ethyl acetate, washed with saturated aqueous common salt solution, dried over Glauber's salt and concentrated. The product was purified by silica gel column chromatography to obtainL 43 g of compound (1-d).

Synthesis of Compound (1-e)

310 ml of methanol and 95 ml of 12 N hydrochloric acid were added to 30.8 g of 2,5-dichloroaniline. An aqueous solution of 13.1 g of sodium nitrite was dropped into the resultant mixture under stirring and under cooling with ice. Since the stirring became unsmooth by a precipitate formed in the course of the addition, the reaction mixture was diluted with a suitable amount of methanol. The mixture was added to a suspension comprising 41.7 g of compound (I-d). 420 ml of methanol and 104 g of sodium acetate under stirring and under cooling with ice. The resultant mixture was poured into water, and crystals thus formed were taken by filtration and dissolved in ethyl acetate. After washing with saturated aqueous common salt solution followed by drying over Glauber's salt and concentration, the product was purified by silica gel column chromatography to obtain 56.2 g of compound (1-e).

Synthesis of Compound (D-30)

55.8 g of compound (1-e) and 0.5 g of 10% palladium carbon were added to 200 ml of methanol, and they were brought into contact with hydrogen in an autoclave for 2 hours. Then the catalyst was filtered out by using Celite as a filter aid. The filtrate was added dropwise to a solution of 36.8 g of 1,5-naphthalenedisulfonic acid tetrahydrate in methanol. The crystals thus formed were taken by filtration to obtain 30. 2 g of 1,5-naphthalenedisulfonate of the intended compound (D-30) in the form of colorless crystals. Melting point: 245 to 251° C. (decomposition).

SYNTHESIS EXAMPLE 2

Compound (D-18) of the present invention as mentioned above was synthesized according to the following scheme:

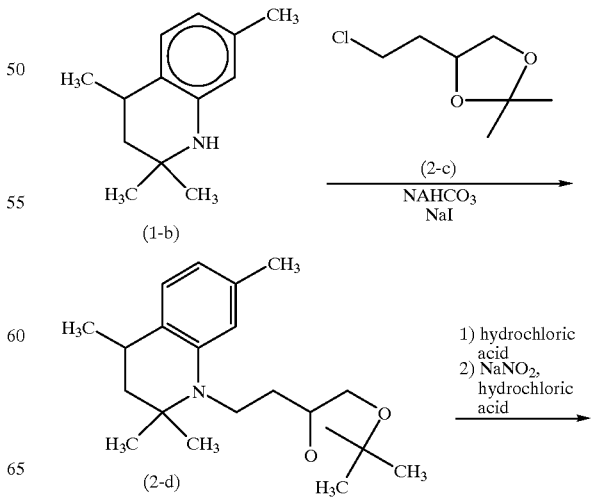

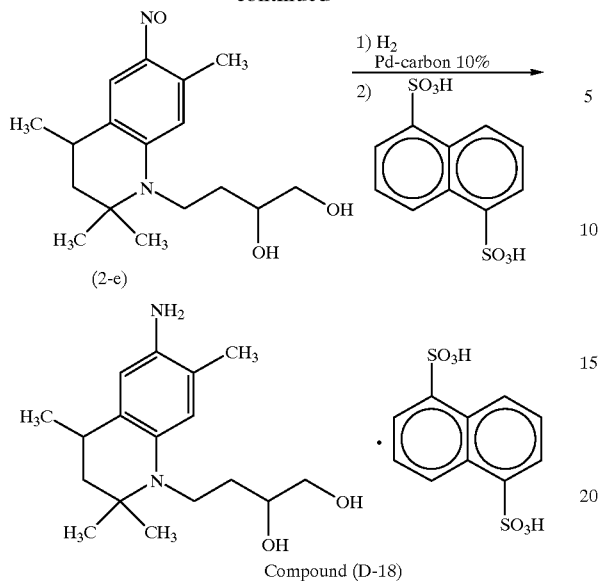

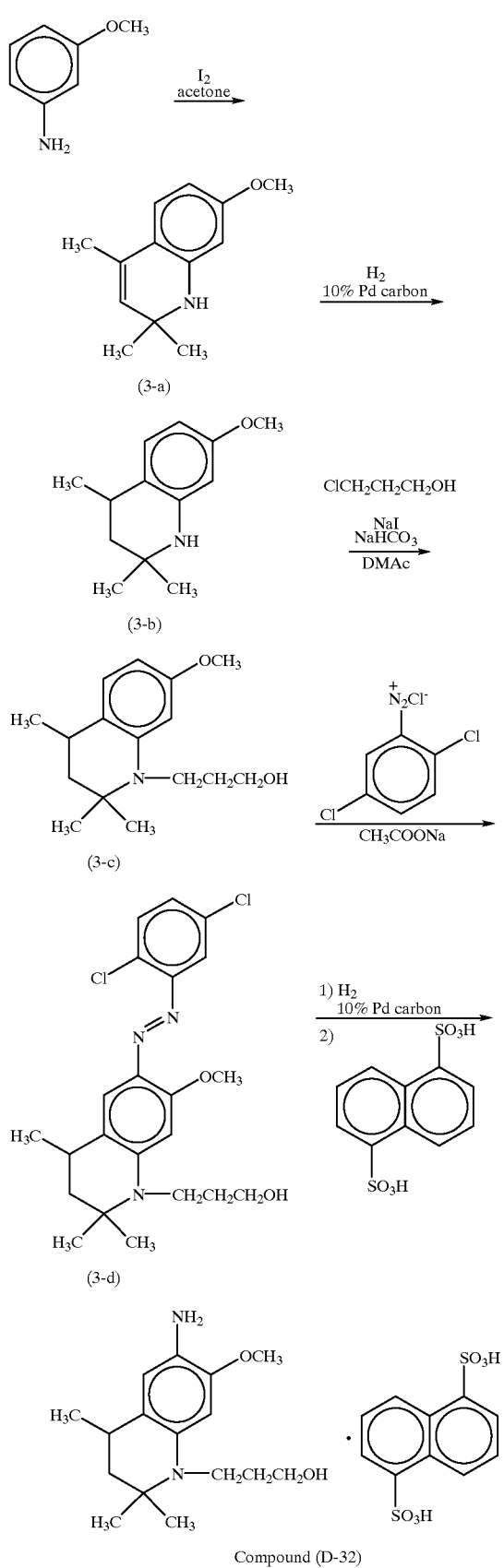

Synthesis of Compound (2-d)

150 ml of N,N-dimethylacetamide, 98.8 g of compound (2-c), 76.0 g of sodium hydrogencarbonate and 45.0 g of sodium iodide were added to 56.8 g of compound (1-b), and the resultant mixture was stirred at 130° C. for 12 hours. The mixture was poured into water, extracted with ethyl acetate, washed with saturated aqueous common salt solution, dried over Glauber's salt and concentrated. The obtained residue was purified by silica gel column chromatography to obtain 88.8 g of compound (2-d).

Synthesis of Compound (2-e)

450 ml of methanol was added to 88.8 g of compound (2-d) to obtain a solution. 79.3 ml of concentrated hydrochloric acid was added dropwise to the solution under cooling with ice for 10 min. After stirring for 5 hours, a solution of 21.3 g of sodium nitrite in 40 ml of water was dropped for 15 minutes, and the resultant mixture was stirred for 1 hour. 1 l of ethyl acetate and 1 l of water, and then 90 g of sodium hydrogencarbonate were added to the mixture. After stirring the resultant mixture, the extraction was conducted. The obtained ethyl acetate layer was washed with saturated aqueous common salt solution, dried over Glauber's salt and concentrated. The obtained residue was purified by silica gel column chromatography to obtain 55.3 g of compound (2-e).

Synthesis of Compound (D-18)

55.3 g of compound (2-e) and 1.0 g of 10% palladium carbon were added to 200 ml of methanol. The resultant mixture was brought into contact with hydrogen in an autoclave for 2 hours. The catalyst was filtered out by using Celite as the filter aid. A solution of 64.8 g of 1,5-naphthalenedisulfonic acid tetrahydrate was dropped into the filtrate. The crystals thus formed were taken by filtration to obtain 88.0 g of 1,5-naphthalenedisulfonate of the intended compound (D-18) in the form of colorless crystals. Melting point: 264 to 267° C. (decomposition).

SYNTHESIS EXAMPLE 3

Compound (D-32) of the present invention as mentioned above was synthesized according to the following scheme:

Synthesis of Compound (3-a)

147 g of compound (3-a) was obtained from 202 g of m-anisidine by a process described on page 328 of Organic Syntheses Collective Volume, Vol. III.

Synthesis of Compound (3-b)

250 ml of ethanol was dissolved in 74.6 g of compound (3-a). 0.85 g of 10% palladium carbon was added to the solution, and the resultant mixture was brought into contact with hydrogen in an autoclave for 9 hours. Then the catalyst was filtered out by using Celite as the filter aid, and the filtrate was concentrated to obtain 69.1 g of compound (3-b).

Synthesis of Compound (3-c)

252 ml of N,N-dimethyl acetamide, 145 g of 3-chloro-1-propanol, 27.1 g of sodium hydrogencarbonate and 48.4 g of sodium iodide were added to 63.1 g of compound (3-b), and the resultant mixture was stirred at 100° C. for 3 hours. The mixture was poured into water, and extracted with ethyl acetate. The extract was washed with saturated common salt solution, dried over Glauber's salt, concentrated and purified by silica gel column chromatography to obtain 82.0 g of compound (3-c).

Synthesis of Compound (3-d)

554 ml of methanol and 142 ml of 12 N hydrochloric acid were added to 55.4 g of 2,5-dichloroaniline. An aqueous solution of 23.6 g of sodium nitrite was added dropwise to the resultant mixture under stirring under cooling with ice. Since the stirring became unsmooth by a precipitate formed in the course of the addition, the reaction mixture was diluted with a suitable amount of methanol. The mixture was added to a suspension comprising 82.0 g of compound (3-c), 820 ml of methanol and 204 g of sodium acetate under stirring and under cooling with ice. The resultant mixture was poured into water, and crystals thus formed were taken by filtration and dissolved in ethyl acetate. After washing with saturated aqueous common salt solution followed by drying over Glauber's salt and concentration, the product was purified by silica gel column chromatography and then recrystallized from acetonitrile to obtain 35.3 g of compound (3-d).

Synthesis of Compound (D-30)

35.0 g of compound (3-d) and 0.5 g of 10% palladium carbon were added to a mixed solvent comprising 35 ml of ethyl acetate and 35 ml of ethanol, and they were brought into contact with hydrogen in an autoclave for 2 hours. Then the catalyst was filtered out by using Celite as a filter aid. The filtrate was added dropwise to a solution of 26.0 g of 1,5-naphthalenedisulfonic acid tetrahydrate in methanol. The crystals thus formed were taken by filtration to obtain 37.5 g of 1,5-naphthalenedisulfonate of the intended compound (D-32) in the form of colorless crystals. Melting point: 253 to 263° C. (decomposition).

SYNTHESIS EXAMPLE 4

Compound (D-37) of the present invention as mentioned above was synthesized according to the following scheme:

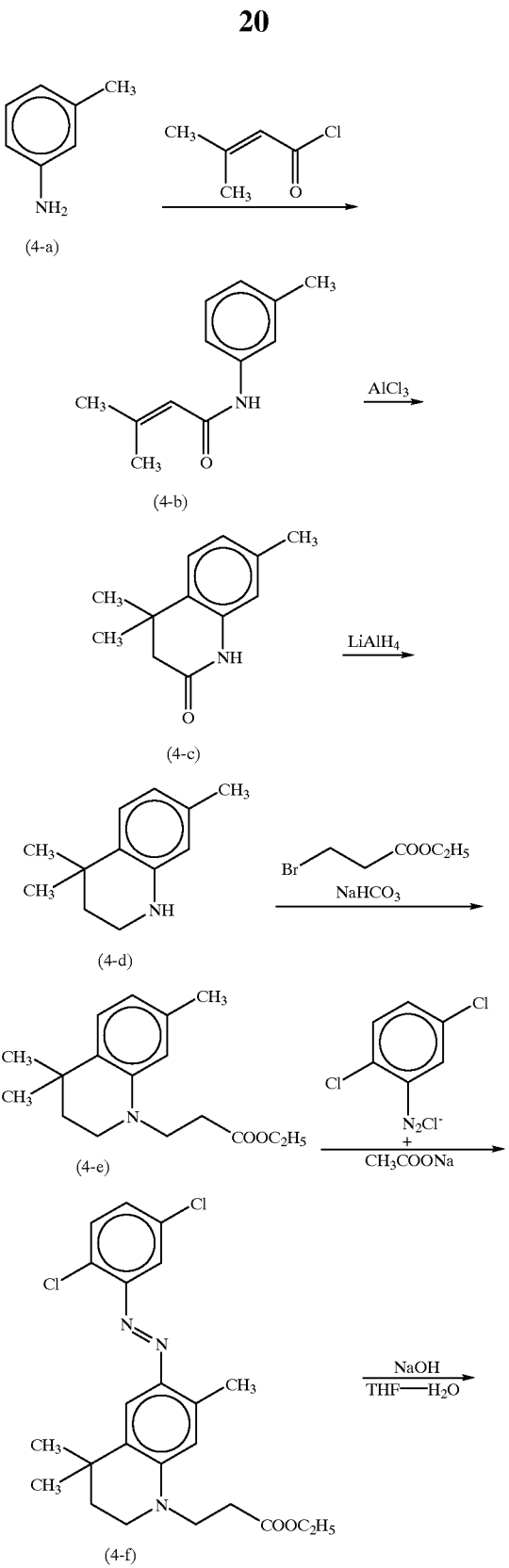

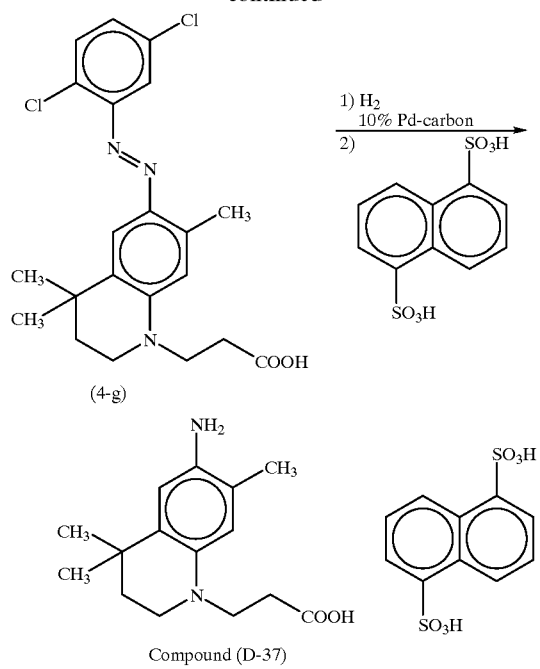

(4-g)

Compound (D-37)

Synthesis of Compound (4-b)

200 ml of acetonitrile and 80 ml of N, N-dimethyl acetamide were added to 105 g of 3-methylcrotonic acid and then 80.5 ml of thionyl chloride was added dropwise to the resultant mixture under stirring under cooling with ice. The stirring continued for one hour. The resultant was added dropwise to 107 g of (4-a) at 20° C. under stirring, after which 162 ml of pyridine was added dropwise to the resultant at 18° C. under stirring. The resultant was poured into water and the precipitate was filtered out to obtain 183 g of (4-b).

Synthesis of Compound (4-c)

Methylene chloride was added to 177 g of (4-b) and 137 g of aluminum chloride was further added thereto under stirring under cooling with ice. The temperature of the reaction system was adjusted to a room temperature, after which 137 g of aluminum chloride was added thereto. After stirring continued for 30 minutes, the resultant was poured into ice water, extracted with ethyl acetate and concentrated. The residue was recrystallized from acetonitrile to obtain 49 g of (4-c).

Synthesis of Compound (4-d)

48.3 g of (4-c) dissolved in 200 ml of THF was added dropwise to a suspension of 11.6 g of lithium aluminum hydride in 150 ml of THF at heat reflux. Then ethyl acetate and methanol were added and further a saturated Glauber's salt solution added thereto to filter out the precipitate using Celite as the filter aid. The thus-obtained residue was concentrated and purified by silica gel column chromatography to obtain 38 g of (4-d).

Synthesis of Compound (4-e)

100 ml of N, N-dimethyl acetamide and 54.8 g of sodium hydrogen carbonate were added to 38 g of (4-d) and the resultant was heated to the temperature range of 120 to 130° C. 117 g of 3-bromo ethylpropionate was added dropwise thereto and stirred for 10 hours. Thereafter, 18.3 g of sodium hydrogen carbonate and 39.3 g of 3-bromo ethylpropionate further added thereto and heated at 150° C. for 4 hours. The resultant was added to water to extract it with ethyl acetate and concentrated. The resultant was purified by silica gel column chromatography to obtain 44.7 g of a mixture of (4-e) and (4-d).

Synthesis of Compound (4-f)

2000 ml of methanol and 271 ml of 12 N hydrochloride were added to 104 g of 2, 5-dichloroaniline and to the resultant there were added aqueous solution of 44.9 g of sodium nitrite dissolved in water under stirring under cooling with ice. The resultant was added to a suspension under stirring under cooling with ice, the suspension being obtained by adding 200 ml of methanol, 400 ml of THF and 267 g of sodium acetate to 44.7 g of a mixture of (4-e) and (4-d). Thereafter, the resultant was poured into water to extract with ethyl acetate and concentrate. Acetone was added to the resulting residue to filter insoluble matter off and the filtrate was concentrated. Thereafter, the resultant was purified by silica gel column chromatography to obtain precipitated crystals by the filtration and dissolved in ethyl acetate. After washing with saturated aqueous common salt solution followed by drying over Glauber's salt and concentration, the product was purified by silica gel column chromatography to obtain 57.5 g of compound (4-f).

Synthesis of Compound (4-g)

An aqueous solution of 450 ml of THF and 21.1 g of sodium hydroxide dissolved in 300 ml of water was added to 54.9 g of (4-f) and stirred at 45° C. for 3 hours. 40.6 ml of 12 N hydrochloric acid was added thereto and concentrated. The thus-obtained residue was extracted with ethyl acetate and concentrated. The resultant was purified by silica gel column chromatography to obtain 49.5 g of compound (4-g).

Synthesis of Compound (D-37)

49.5 g of compound (4-g) and 1.0 g of 10% palladium carbon were added to 500 ml of ethanol and they were brought into contact with hydrogen in an autoclave at a room temperature for 2 hours. Then 200 ml of THF and 1.0 g of 10% palladium carbon were further added thereto and they were brought into contact with hydrogen at 35° C. for 4 hours. At that time, precipitates were observed in the reaction system. Thereafter, 42.5 g of 1,5-naphthalene disulfonic acid tetrahydrate, water and ethyl acetate were added thereto, and the catalyst was filtered out by using Celite as a filter aid. The thus-obtained water phase was concentrated and the resulting precipitated crystals were obtained by the filtration. Water was added to the resulting crystals and subjected to heat reflux followed by adding methanol thereto to obtain by filtration 45.5 g of 1,5-naphthalenedisulfonate of the intended compound (D-37) in the form of colorless crystals. Melting point: 260 to 270° C. (decomposition).

SYNTHESIS EXAMPLE 5

Compound (D-39) of the present invention as mentioned above was synthesized according to the following scheme:

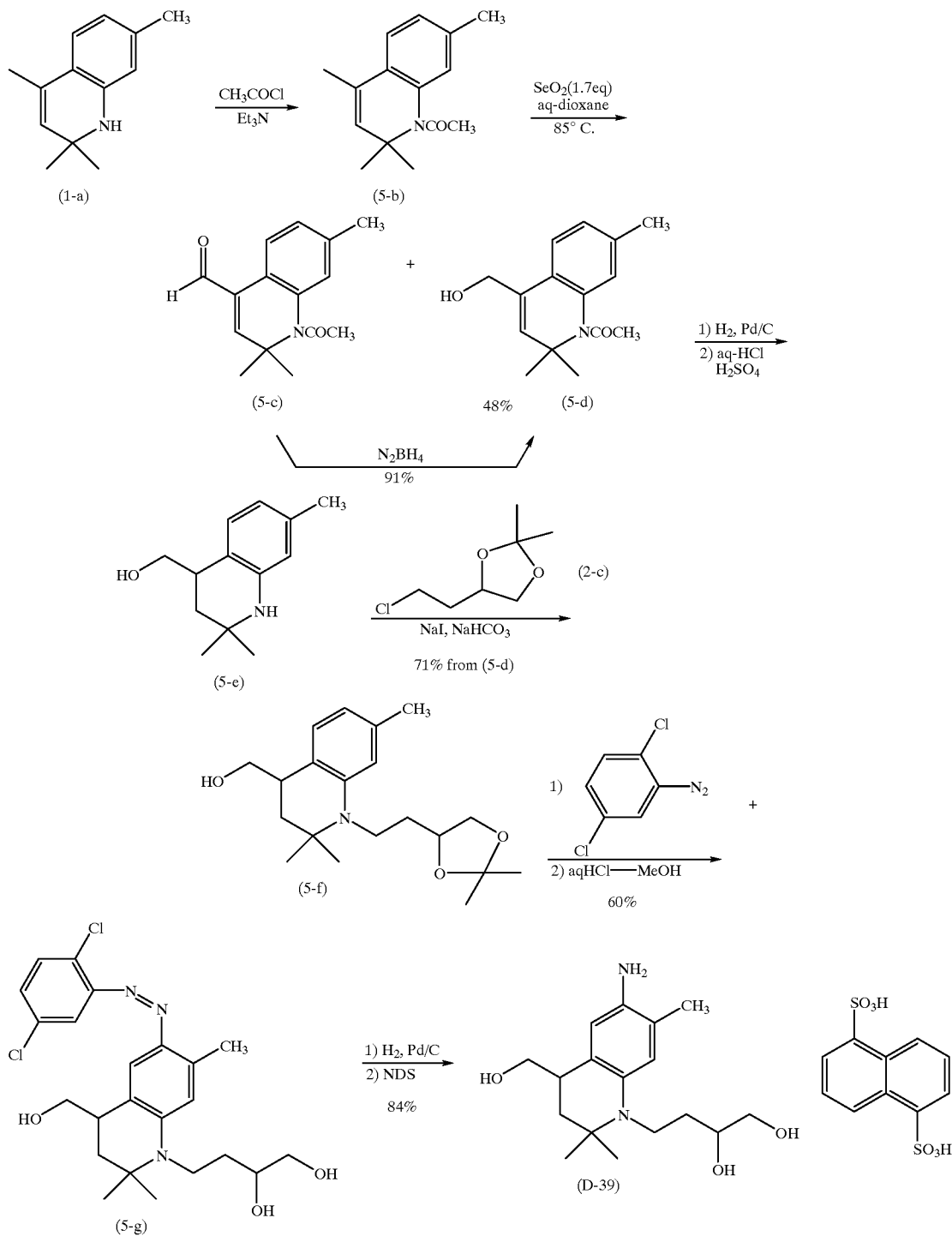

Synthesis of Compound (5-b)

180 ml of DMAC was added to 56.2 g of (1-a) and 23.5 ml of acetyl chloride was added dropwise thereto in 10 minutes under stirring under cooling with ice. After stirring for another 10 minutes, 46.0 ml of triethylamine was added dropwise thereto for 10 minutes. The resultant was stirred for 1 hour and then extracted with ethyl acetate, washed with water and concentrated. The resultant was purified by silica gel column chromatography to obtain 36.0 g of compound (5-b) at 52% yield.

Synthesis of Compound (5-d)

33.7 g of (5-b) was dissolved in 150 ml of dioxane and an aqueous solution of 27.1 g of selenium dioxide and 40 ml of water was added thereto at a room temperature under stirring. After stirring it for 10 minutes at a room temperature, the stirring was continued at a temperature of 85° C. for 5 hours. The resultant was extracted with ethyl acetate (inorganic materials were filtered off using Celite), washed with water and concentrated. The resultant was purified by column chromatography to obtain 18.6 g of compound (5-d) at 48% yield. At the same time, 17.4 g of compound (5-c) was obtained.

17.4 g of compound (5-c) was added to a mixture of 20 ml of THF and 40 ml of ethanol, and 2.70 g of sodium boron hydride was added thereto in 5 minutes under stirring under cooling with ice. After stirring for another 10 minutes, the reaction mixture was poured onto ice and 31 ml of conc. hydrochloric acid was added thereto under stirring followed by adding 5 ml of ammonium solution thereto. The resultant was extracted with ethyl acetate, washed with water and concentrated. The resultant was purified by silica gel column chromatography to obtain 16.9 g of compound (5-d) at 91% yield.

Synthesis of Compound (5-f)

35.5 g of (5-d) was dissolved in 100 ml of ethanol and 3 g of Raney nickel to stir it in an autoclave at 50° C. for 5 hours under 50 kg/cm$^2$ of hydrogen pressure. The resultant was filtered using Celite, concentrated and 90 ml of ethanol was added thereto to dissolve it. 20 ml of conc. hydrochloric acid was added thereto and the resultant was stirred at heat reflux. 10 minutes later, 13.2 ml of sulfuric acid was added dropwise thereto and continued to do the heat reflux for 2 hours. After cooling it to a room temperature, the resultant was poured onto ice, neutralized with sodium bicarbonate, extracted with ethyl acetate, washed with water and concentrated to obtain (5-e).

The thus-obtained concentrated residue was dissolved in 50 ml of DMAC, and 79 g of sodium bicarbonate and 18.0 g of sodium iodide were added thereto to heat it at 120° C. under stirring followed by adding dropwise 77.0 g of (2-c) thereto in 20 minutes. After heating and stirring for another 3 hours, the resultant was cooled to a room temperature, extracted with ethyl acetate, washed with water and concentrated. The resultant was purified by column chromatography to obtain 34.3 g of compound (5-f) at 71% yield.

Synthesis of Compound (5-g)

39.6 g of dichloroaniline was dissolved in 600 ml of methanol, and 105 ml of conc. hydrochloric acid was added thereto under stirring under cooling with ice. An aqueous solution of 18.6 g of sodium nitrite and 20 ml of water was added dropwise thereto in 10 minutes, maintaining the temperature of the reaction system at 15° C. or lower, so as to prepare a diazonium salt solution. On the other hand, 27.2 g of (5-f) was dissolved in a mixed solvent of 300 ml of THF and 150 ml of methanol, and 134 g of sodium acetate was added thereto under stirring under cooling with ice. The previously prepared diazonium salt solution was added thereto in 20 minutes, maintaining the temperature of the reaction system at 15° C. or lower. After stirring for another 30 minutes, the resultant was extracted with ethyl acetate (a filtration using Celite was conducted since a by-product was precipitated as crystal), washed with water, concentrated and purified by column chromatography to obtain 32.9 g of azo dye. The thus-obtained azo dye was dissolved in 120 ml of methanol and 16.7 ml of conc. hydrochloric acid was added thereto under stirring under cooling with ice followed by stirring it for 1 hour while returning the temperature of the reaction system to a room temperature. The resultant was poured onto ice, neutralized with sodium bicarbonate, extracted, washed with water and concentrated. The resulting residue was subjected to acetonitrile crystallization to obtain 22.8 g of (5-g) at 60% yield.

Synthesis of Compound (D-39)

22.8 g of compound (5-g) and 2.0 g of 10% palladium carbon were added to 70 ml of ethanol and they were agitated in an autoclave for 4 hours under a hydrogen pressure of 50 kg/cm$^2$. The resultant was filtered using Celite, and to the resulting filtrate there was added a solution of 17.6 g of 1,5-naphthalene disulfonic acid dissolved in 50 ml of ethanol followed by stirring it for 10 minutes. The resultant was concentrated and dissolved with 50 ml of water and 50 ml of ethyl acetate, after which it was subjected to the liquid separation procedure. The thus-obtained water phase was concentrated and crystallized with methanol to obtain 24.4 g of compound (D-39) at 84% yield.

NMR (D$_2$O, mixture of diastereomers): 8.86 (d, J=10.0 Hz, 2H) 8.22 (d, J=10.0 Hz, 2H), 7.74 (dd, J=10.0, 10.0 Hz, 2H), 7.46 (s, 1H), 7.23, 7.20 (s, total 1H), 2.9–3.9 (m, 8H), 2.34 (s, 3H), 1.5–2.2 (m, 6H), 1.52, 1.50 (s, total 3H), 1.00, 1.02 (s, total 3H).

The color developing agent of the present invention can be used either singly or in combination with other known p-phenylenediamine derivatives. Typical examples of the compounds which can be used in combination with the color developing agent include the following compounds, which by no means limit them:

P-1: N,N-diethyl-p-phenylenediamine,

P-2: 4-amino-3-methyl-N,N-diethylaniline,

P-3: 4-amino-3-methyl-N-ethyl-N-(3-hydroxypropyl) aniline,

P-4: 4-amino-N-ethyl-N-(2-hydroxyethyl)aniline,

P-5: 4-amino-3-methyl-N-ethyl-N-(2-hydroxyethyl) aniline,

P-6: 4-amino-3-methyl-N-ethyl-N-2-(methanesulfonamidoethyl)aniline,

P-7: N-(2-amino-5-N,N-diethylaminophenylethyl) methane sulfonamide,

P-8: N,N-dimethyl-p-phenylenediamine,

P-9: 4-amino-3-methyl-N-ethyl-N-(2-methoxyethyl) aniline,

P-10: 4-amino-3-methyl-N-ethyl-N-(4-hydroxybutyl) aniline, and

P-11: 4-amino-3-methyl-N-ethyl-N-(2-butoxyethyl) aniline.

Among the above-described p-phenylenediamine derivatives to be used for the combination, particularly preferred are compounds P-3, P-5, P-6 and P-10. The p-phenylenediamine derivatives are usually used in the form of their salts such as sulfates, hydrochlorides, sulfites, p-toluenesulfonates, nitrates and naphthalene-1,5-disulfonates.

The processing composition of the present invention may be in liquid form or solid form (such as powdery or granular form).

These compounds can be used in combination of two or more of them depending on the purpose. The aromatic primary amine developing agent is used in an amount of preferably about 0.001 to 0.2 mol, more preferably 0.005 to 0.1 mol, per liter of the color developer.

The color developer of the present invention may contain a compound for directly preserving the above-described aromatic primary amine color developing agent, which is selected from among hydroxylamines described in J.P.

KOKAI Nos. Sho 63-5341, Sho 63-106655 and Hei 4-144446, hydroxamic acids described in J.P. KOKAI No. Sho 63-43138, hydrazines and hydrazides described in J.P. KOKAI No. Sho 63-146041, phenols described in J.P. KOKAI Nos. Sho 63-44657 and Sho 63-58443, α-hydroxyketones and α-aminoketones described in J.P. KOKAI No. Sho 63-44656, and saccharides described in J.P. KOKAI No. Sho 63-36244. Such a compound can be used in combination with monoamines described in J.P. KOKAI Nos. Sho 63-4235, 63-24254, 63-21647, 63-146040, 63-27841 and 63-25654, diamines described in J.P. KOKAI Nos. Sho 63-30845, 63-14640 and 63-43139, polyamines described in J.P. KOKAI Nos. Sho 63-21647, 63-26655 and 63-44655, nitroxy radicals described in J.P. KOKAI No. Sho 63-53551, alcohols described in J.P. KOKAI Nos. Sho 63-43140 and 63-53549, oximes described in J.P. KOKAI No. Sho 63-56654 and tertiary amines described in J.P. KOKAI No. Sho 63-239447.

The color developer may contain, if necessary, also a preservative such as metals described in J.P. KOKAI Nos. Sho 57-44148 and 57-53749, salicylic acids described in J.P. KOKAI No. Sho 59-180588, alkanolamines described in J.P. KOKAI No. Sho 54-3582, polyethyleneimines described in J.P. KOKAI No. Sho 56-94349 and aromatic polyhydroxy compounds described in U.S. Pat. No. 3,746,544. Particularly when the hydroxylamines are used, they are preferably used in combination with the above-described alkanolamines or aromatic polyhydroxy compounds.

Particularly preferred preservatives are hydroxylamines represented by general formula (I) given in J.P. KOKAI No. Hei 3-144446. Among them, compounds having methyl, ethyl, sulfo or carboxy group are preferred. The preservative is used in an amount of 20 to 200 mmol, preferably 30 to 150 mmol, per liter of the color developer.

The color developer of the present invention may further contain additives mentioned in the above-described J.P. KOKAI No. Hei 3-144446. For example, a compound selected from among carbonates, phosphates, borates and hydroxybenzoates mentioned on page 9 of the JP Kokai thereof can be used as a buffering agent for maintaining pH. The pH of the color developer is kept preferably in the range of 9.0 to 12.5, more preferably in the range of 9.5 to 11.5.

Antifoggants usable herein are halide ions and organic antifoggants mentioned on page 10 of the above-mentioned JP Kokai. Particularly when the concentration of the color developing agent in the color developer is as high as 20 mmol/l or above or when the processing temperature is as high as 40° C. or above, a considerably high bromide ion concentration, i.e., 17 to 60 mmol/l is preferred. If necessary, the concentration can be controlled in a preferred range by removing the halogen with an ion exchange resin or ion exchange membrane.

The chelating agents preferably used herein are aminopolycarboxylic acids, aminopolyphosphonic acids, alkylphosphonic acids and phosphonocarboxylic acids. For example, there can be used ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and salts of them. Preferred chelating agents are biodegradable compounds such as those mentioned in J.P. KOKAI Nos. Sho 63-146998, 63-199295, 63-267750 and 63-267751 and Hei 2-229146 and 3-186841, German Patent No. 3739610 and European Patent No. 468325.

Furthermore, the color developer of the present invention may contain, if necessary, a development restrainer such as a benzimidazole, benzothiazole or mercapto compound; a development accelerator such as a benzyl alcohol, polyethylene glycol, quaternary ammonium salt or amine; a dye-forming coupler; a competitive coupler; an assistant developing agent such as 1-phenyl-3-pyrazolidone; a tackifier; and a surfactant such as an alkylsulfonic acid, arylsulfonic acid, aliphatic carboxylic acid or aromatic carboxylic acid.

When the color developer of the present invention is used for processing a photographic photosensitive material, it is replenished in an amount of preferably 550 ml or below, more preferably 450 ml of below, most preferably 80 to 400 ml, per $m^2$. By reducing bromide ion in the replenisher or by using no bromide ion, the amount thereof can be reduced to 300 ml or below.

The processing temperature for the color developer is preferably 35° C. or above, more preferably 40 to 50° C.

The processing time for the color developer is preferably not longer than 3 minutes and 15 seconds, more preferably 30 seconds to 2 minutes and 30 seconds.

It is preferred to inhibit the evaporation of the developer and oxidation thereof by air. The contact area of the processing liquid with air in the processing vessel can be represented by the opening rate defined as follows:

Opening rate=[(contact area of processing solution with air $(cm^2)$]/ [volume of processing solution $(cm^3)$]

The opening rate $(cm^{-1})$ defined as above is preferably not higher than 0.05, more preferably in the range of 0.0005 to 0.01. The opening rate is reduced by covering the surface of the photographic processing solution in the processing vessel with a floating lid or the like, by providing a movable lid as described in J.P. KOKAI No. Hei 1-82033 or by a slit development process described in J.P. KOKAI No. Sho 63-216050. It is preferred that the processing solution in a color developer-replenishing tank or in a processing tank is sealded with a high-boiling organic solvent or a high-molecular compound to reduce the contact area thereof with air. It is particulrly preferred to use liquid paraffin, an organosiloxane or the like.

The opening rate can be reduced not only in the color development and black-and-white development steps but also in all of the subsequent steps such as bleaching, bleach-fixing, fixing, water washing and stabilization steps.

The developer can be reused by regeneration. The term "regeneration of the developer" herein indicates that the used developer is treated with an anion exchange resin or by electrodialysis and that the activity of the developer is increased by adding a processing agent called "regenerating agent". The regeneration rate (rate of the overflown solution in the replenisher) is preferably at least 50%, particularly at least 70%.

The regeneration is conducted preferably with the anion exchange resin. Particularly preferred composition of the anion exchange resin and method for regeneration of the resin are those described in "Diaion Manual" (Edition 14, 1986) published by Mitsubishi Chemical Industries Ltd. Among the anion exchange resins, preferred are those described in J.P. KOKAI Nos. Hei 2-952 and 1-281152.

In the present invention, the color-developed photosensitive material is then desilvered. The desilverization process herein basically comprises bleaching process and fixing process. Both processes can be conducted at the same time by a bleach-fixing process or these processes are combined with each other.

The preferred bleaching agents are ferric aminopolycarboxylates and salts of them as described on page 11 of the above-mentioned J. P. KOKAI No. Hei 3-144446. Examples of them include ferric salts of ethylenediaminetetraacetic acid, diethylenetriaminepentaacetic acid, cyclohexanediaminetetraacetic acid, methyliminodiacetic acid, 1,3-diaminopropanetetraacetic acid and glycol ether diaminetetraacetic acid. Other bleaching agents include complex salts of citric acid, tartaric acid and malic acid. Among them, particularly preferred are iron (III) complex salts of aminopolycarboxylic acids such as iron (III) complex salt of ethylenediaminetetraacetic acid and iron (III) complex salt of 1,3-diaminopropanetetraacetic acid. Such an iron (III) complex salt of aminopolycarboxylic acid is particularly effective in both bleaching solution and bleach-fixing solution.

The bleaching solution, bleach-fixing solution, and preceding bath thereof may contan a bleaching accelerator, if necessary. Examples of the bleaching accelerators include compounds having a mercapto group or disulfido group described in U.S. Pat. No. 3,893,858, West German Patent Nos. 1,290,812 and 2,059,988, J.P. KOKAI Nos. Sho 53-32736, 53-57831, 53-37418, 53-72623, 53-95630, 53-95631, 53-104232, 53-124424, 53-141623 and 53-28426 and Research Disclosure No. 17129 (July, 1978); thiazolidine derivatives described in J.P. KOKAI No. Sho 50-140129; thiourea derivatives described in Japanese Patent Publication for Opposition Purpose (hereinafter referred to as "J.P. KOKOKU") No. Sho 45-8506, J.P. KOKAI Nos. Sho 52-20832 and 53-32735 and U.S. Pat. No. 3,706,561; iodides described in West German Patent No. 1,125,715 and J.P. KOKAI No. Sho 58-16235; polyoxyethylene compounds described in West German Patent Nos. 966,410 and 2,748,430; polyamine compounds described in J.P. KOKOKU No. Sho 45-8836; compounds described in J.P. KOKAI Nos. Sho 49-40943, 49-59644, 53-94927, 54-35727, 55-26506 and 58-163940; and bromide ions. Among them, compounds having a mercapto group or disulfido group are preferred in view of the remarkable accelerating effect. Particularly preferred are compounds described in U.S. Pat. No. 3,893,858, West German Patent No. 1,290,812 and J. P. KOKAI No. Sho 53-95630. Further, compounds described in U.S. Pat. No. 4,552,834 are also preferred. These bleach-accelerators may be also added to the photosensitive material. When a color photosensitive material for photography is to be bleach-fixed, these bleaching accelerators are particularly effective.

The desilvering bath of the present invention may contain rehalogenating agents, pH buffering agents and other known additives as described on page 12 of J.P. KOKAI No. Hei 3-144446, in addition to the bleaching agent.

An organic acid is preferably incorporated into the bleaching solution and bleach-fixing solution in order to prevent a bleach stain, in addition to the above-described compounds. Particularly preferred organic acids are those having an acid dissotiation constant (pKa) of 2 to 6 such as acetic acid, propionic acid, hydroxyacetic acid, succinic acid, maleic acid, glutaric acid, fumaric acid, malonic acid and adipic acid. Particularly preferred are succinic, maleic and glutaric acids.

The pH of the bleaching solution and bleach-fixing solution is usually 4.0 to 8.0. For conducting the process more rapidly, pH can be further lowered.

The fixing agents usable for the fixing solution or bleach-fixing solution include, for example, thiosulfates, thiocyanates, thioether compounds, thioureas and a large amount of iodides. Among them, the thiosulfates are commonly used and ammonium thiosulfate is most widely usable. A combination of a thiosulfate with a thiocyanate, thioether compound or thiourea is also preferred.

Examples of preferred preservatives for the fixing solution and bleach-fixing solution include sulfites, hydrogensulfites, carbonylhydrogensulfite adducts and sulfinic acid compounds described in European Patent No. 294769 A. Further, it is preferred to add a chelating agent such as an aminopolycarboxylic acid or organic phosphonic acid to the fixing solution or bleach-fixing solution in order to stabilize it. Examples of preferred chelating agents include 1-hydroxyethylidene-1,1-diphosphonic acid, ethylenediamine-N,N,N,N'-tetrakis(methylenephosphonic acid), nitrilotrimethylenephosphonic acid, ethylenediaminetetraacetic acid, diethylenetriaminepentaacetic acid, cyclohexanediaminetetraacetic acid and 1,2-propylenediaminetetraacetic acid. Among them, 1-hydroxyethylidene-1,1-diphosphonic acid and ethylenediaminetetraacetic acid are particularly preferred.

It is preferred to incorporate a compound having a pKa of 6.0 to 9.0 such as imidazole, 1-methylimidazole, 1-ethylimidazole or 2-methylimidazole into the fixing solution or bleach-fixing solution in order to adjust pH thereof.

The imidazole compounds herein indicate imidazole and derivatives thereof. Preferred substituents of imidazole include, for example, alkyl, alkenyl, alkynyl, amino and nitro groups and halogen atoms. The alkyl, alkenyl and alkynyl groups may be further substituted with an amino or nitro group or a halogen atom. The total carbon number of the substituents of imidazole is preferably 1 to 6. The most preferred substituent is methyl group.

Examples of the imidazole compounds will be given below, which by no means limit them:

imidazole
1-methylimidazole
2-methylimidazole
4-methylimidazole
4-(2-hydroxyethyl)-imidazole
2-ethylimidazole
2-vinylimidazole
4-propylimidazole
4-(2-aminoethyl)imidazole
2,4-dimethylimidazole, and
2-chloroimidazole.

Among them, preferred are imidazole; 2-methylimidazole and 4-methylimidazole, and most preferred is imidazole.

When a replenishing system is employed in the process of the present invention, the quantity of the fixing solution or bleach-fixing solution to be replenished is preferably 100 to 3,000 ml, more preferably 300 to 1800 ml, per $m^2$ of the photosensitive material. The bleach-fixing solution can be replenished by using a bleach-fixing replenisher or, as described in J.P. KOKAI No. Sho 61-143755 or Japanese Patent Application No. Hei 2-216389, overflowing bleaching solution and fixing solution can be used.

The total processing time in the desilvering step comprising bleaching, bleach-fixing and fixing in the present invention is preferably 30 seconds to 3 minutes, more preferably 45 seconds to 2 minutes. The processing temperature is 30 to 60° C., preferably 35 to 55° C.

In processing with a processing solution having a bleaching effect, it is particularly preferred to conduct aeration so as to keep the photographic properties very stable in the present invention. The aeration can be conducted by a method known in the art, such as blowing of air into the solution having the bleaching effect or absorption of air with an ejector.

In the blowing of air, it is preferred to release air in the solution by means of a diffusing tube having fine pores. Such a type of diffusing tube is widely used for an aeration tank in the treatment of an activated sludge. In the aeration, techniques described on pages BL-1 to BL-2 of Z-121, Using Process C-41 (the third edition) published by Eastman Kodak Co. in 1982 can be employed. In the process of the present invention with the processing solution having bleaching effect, vigorous stirring is preferred. For the stirring, contents of J. P. KOKAI No. Hei 3-33847 (from line 6, right upper column to line 2, left lower column on page 8) can be employed as they are.

Silver can be recovered from the processing solution having the fixing effect of the present invention by a well-known method, and the regenerated solution is usable. Silver can be recovered by an electrolysis method (French Patent No. 2,299,667), precipitation method (J. P. KOKAI No. Sho 52-73037 and German Patent No. 2,331,220), ion exchange method (J. P. KOKAI No. Sho 51-17114 and German Patent No. 2,548,237) and metal replacement method (British Patent No. 1,353,805). In these methods, silver is preferably recovered in line from the tank solution so as to improve the rapidness.

The processing solution of the present invention having the bleaching effect is reusable by recovering the overflow used in the process and adding the components to regulate the composition thereof. Such a regeneration is easy in the present invention. The details of the regeneration are described on pages 39 to 40 of Fuji Film Processing Manual, Fuji Color Negative Film, CN-16 Process (revised in August, 1990) published by Fuji Photo Film Co., Ltd.

Although the kit for preparing the processing solution of the present invention having the bleaching effect may be in the form of either liquid or powder, the powder is more easily prepared than the liquid, since most starting materials are in powder having only a slight hygroscopicity after removal of ammonium salts.

Further, the kit for the regeneration is preferably in the form of a powder from the viewpoint of reduction in the quantity of waste water, since it can be directly added without using excess water.

For the regeneration of the processing solution having the bleaching function, a method described in "Shashin Kogaku no Kiso,—Gin'en Shashin Hen-(The Fundamentals of Photographic Engineering,—Edition of Silver Salt Photographs—)" (edited by Nihon Shashin Gakkai and published by Corona in 1979) can be employed in addition to the above-described aeration method. In particular, the bleaching solution can be regenerated by an electrolytic regeneration method or a method wherein hydrobromic acid, chlorous acid, bromine, a bromine precursor, a persulfate, and hydrogen peroxide, or a combination of a catalyst with hydrogen peroxide, bromous acid or ozone is used.

In the electrolytic regeneration method, a cathode and an anode are placed in the same bleaching bath, or the anodic bath is separated from the cathodic bath with a diaphragm. In another electrolytic regeneration method, the bleaching sollution and developer and/or fixing solution can be regenerated at the same time by using a diaphragm.

The fixing solution and bleach-fixing solution are regenerated by electrolytically reducing silver ion accumulated therein. To maintain the fixing function, it is also preferred to remove the accumulated halogen ion with an anion exchange resin.

In the desilverizing steps, the stirring is conducted preferably as vigorously as possible by, for example, a method which comprises bumping a jet of the processing solution against the emulsion surface of the photosensitive material as described in J. P. KOKAI No. Sho 62-183460; a method wherein the stirring effect is improved with a rotating means as described in J. P. KOKAI No. Sho 62-183461; a method wherein the photosensitive material is moved while the emulsion surface thereof is brought into contact with a wiper blade provided in the solution so as to make the flow on the emulsion surface turbulent and thereby improving the effect of the stirring; and a method wherein the quantity of the circulating flow of the whole processing solutions is increased. Such a means of making the stirring vigorous is effective for any of the bleaching solution, bleach-fixing solution and fixing solution. Supposedly, the improvement in the stirring effect accelerates the feeding of the bleaching agent and fixing agent into the emulsion membrane, thereby increasing the desilverizing speed. The above-described means of improving the stirring effect are more effective when a bleaching accelerator is used. In such a case, the acceleration effect is further improved and inhibition of the fixing by the bleaching accelerator can be controlled.

An automatic developing machine used for developing the photosensitive material of the present invention preferably has a means of transporting the photosensitive material as described in J. P. KOKAI Nos. Sho 60-191257, 60-191258 and 60-191259. As described in J. P. KOKAI No. Sho 60-191257, such a transportation means remarkably reduces the amount of the processing solution brought from the preceding bath into a subsequent bath, so that the deterioration in the function of the processing solution can be remarkably prevented. Such a function is particularly effective in reducing the processing time in each step and also in reducing the amount of the replenisher.

After the step of the process having fixing function, the photosensitive material is usually washed with water. Alternatively, a simple method can be employed wherein the material is substantially not washed with water after processing with the solution having the fixing function but it is stabilized with a stabilizing solution.

The amount of water used in the washing step varies in a wide range depending on the properties of the photosensitive material (which depend on, for example, couplers used), temperature of water used for washing, number of the tanks used for washing with water (number of stages), replenishing method such as counter flow or down-flow system and various other conditions. Among them, the relationship between the number of the tanks for washing with water and the amount of water in the multi-stage counter flow system can be determined by a method described in "Journal of the Society of Motion Picture and Television Engineers", Vol. 64, pages 248 to 253 (May, 1955). Two to four stages are preferred. The amount of the solution to be replenished is 1 to 50 times, preferably 1 to 30 times and still preferably 1 to 10 times larger than that brought from the preceding bath per a unit area. A preferred method for efficiently reducing the amount of the replenisher is so-called multi-tank washing method or stabilizing method wherein the water washing tank or stabilizing tank is divided with a diaphragm so that the photosensitive material is processed in the liquid by passing it through a slit of a wiper blade or the like without being exposed to air.

Although the amount of water necessitated for washing can be remarkably reduced by the multi-stage counter flow method or multi-tank washing method, another problem is caused in this method that bacteria propagate themselves while water is kept for a longer time in the tanks and, as a result, a suspended matter thus formed is attached to the photosensitive material. For solving this problem, a very effective method for reducing the amount of calcium ion and magnesium ion described in J. P. KOKAI No. Sho 62-288, 838 can be employed. Further, this problem can be solved also by using isothiazolone compounds described in J. P. KOKAI No. Sho 57-8,542, thiabendazoles, chlorine-containing germicides such as chlorinated sodium isocyanurates, benzotriazoles and germicides described in Hiroshi Horiguchi "Bokin Bobai-zai no Kagaku (Chemistry for Prevention of Bacteria and Fungi)" published by Sankyo Book Publishing Co. in 1986, "Biseibutsu no Mekkin, Sakkin, Bobai Gijutsu (Technique of Sterilization and Prevention of Microorganisms)" edited by Eisei Gijutsu-kai and published by Kogyo Gijutsu-kai in 1982 and "Bokinbobai-zai Jiten (Dictionary of Sterliers and Antifungal Agents)" edited by Nippon Bokinbobai Gakkai and published in 1986.

The pH of washing water used for processing the photosensitive material of the present invention and a stabilizing solution is 4 to 9, preferably 5 to 8. The temperature and time which vary depending on the properties and use of the photosensitive material are usually 15 to 45° C. and 20 seconds to 10 minutes, preferably 25 to 40° C. and 30 seconds to 5 minutes. The photosensitive material can be processed directly with a stabilizing solution in place of washing with water. The stabilization can be conducted by any of known processes described in J. P. KOKAI Nos. Sho 57-8543, 58-14834 and 60-220345.

The stabilizing solution contains a compound which stabilizes the color image, selected from among, for example, formalin, benzaldehydes such as m-hydroxybenzaldehyde, formaldehyde/bisulfite adduct, hexamethylenetetramine and derivatives thereof, hexahydrotriazine and derivatives thereof, dimethylurea, N-methylol compounds such as N-methylolpyrazole, organic acids and pH buffering agents. The preferred amount of these compounds is 0.001 to 0.02 mol per liter of the stabilizing solution. The free formaldehyde concentration in the stabilizing solution is preferably as low as possible so as to prevent formaldehyde gas from sublimation. From such a point of view as above, preferred color image stabilizers are m-hydroxybenzaldehyde, hexamethylenetetramine, N-methylolazoles described in J. P. KOKAI No. Hei 4-270344 such as N-methylolpyrazole and azolylmethylamines described in J. P. KOKAI No. Hei 4-313753 such as N,N'-bis(1,2,4-triazol-1-ylmethyl) piperazine. Particularly preferred is a combination of an azole such as 1,2,4-triazole with an azolylmethylamine such as 1,4-bis(1,2,4-triazol-1-ylmethyl)piperazine or a derivative thereof as described in J. P. KOKAI No. Hei 4-359249 (corresponding to European Patent Unexamined Published Application No. 519190 A 2), since a high image stability and a low formaldehyde vapor pressure are realized by the combination. The stabilizing solution preferably contains, if necessary, an ammonium compound such as ammonium chloride or ammonium sulfite, a metal compound of Bi and Al, a fluorescent whitening agent, a hardener, an alkanolamine described in U.S. Pat. No. 4,786,583, and a preservative which can be contained in also the above-described fixing solution and bleach-fixing solution such as a sulfinic acid compound described in J. P. KOKAI No. Hei 1-231051.

Various surfactants can be incorporated into washing water and stabilizing solution so as to prevent the unevenness of water spots in the course of drying of the photosensitive material. Among them, preferred is an noionic surfactant, particularly an alkylphenol ethylene oxide adduct. The alkylphenols are particularly preferably octyl-, nonyl-, dodecyl- and dinonylphenols. The molar number of ethylene oxide to be added is particularly preferably 8 to 14. It is also preferred to use a silicon surfactant having a high antifoaming effect.

The washing water and stabilizing solution preferably contain a various kinds of chelating agents. Preferred chelating agents include aminopolycarboxylic acids such as ethylenediaminetetraacetic acid and diethylenetriaminepentaacetic acid; organic phosphonic acids such as 1-hydroxyethylidene-1,1-diphosphonic acid, N,N,N'-trimethylenephosphonic acid and diethylenetriamine-N,N, N',N'-tetramethylenephosphonic acid; and hydrolyzates of maleic anhydride polymers described in European Patent No. 345,172 A 1.

The overflow obtained during the washing with water and/or replenishing of the stabilizing solution is reusable in other steps such as the desilverizing step.

When each of the above-described processing solutions is concentrated by evaporation in the process with an automatic developing machine, it is preferred to replenish a suitable amount of water, correcting solution or process replenisher in order to compensate the solution for concentration caused by the evaporation. Although the method for replenishing water is not particularly limited, preferred are the following methods: a method described in J. P. KOKAI Nos. Hei 1-254959 and 1-254960 wherein a monitor water tank which is different from the bleaching tank is provided, the amount of water evaporated from the monitor water tank is determined, the amount of water evaporated from the bleaching tank is calculated from the determined amount of evaporated water, and water is replenished into the bleaching tank in proportion to the amount of evaporated water; and a method described in J. P. KOKAI Nos. Hei 3-248155, 3-249644, 3-249645 and 3-249646 wherein the compensation for the evaporation is conducted with a liquid level sensor or overflow sensor. Although water for compensating for the evaporation in each processing solution may be tap water, deionized water or sterilized water preferably used in the above-described water washing steps is preferred.

Each processing solution is used at 10 to 50° C. in the present invention. Although the standard temperature ranges from 33 to 38° C., it is also possible to accelerate the process and thereby to reduce the process time at a higher temperature or, on the contrary, to conduct the process at a lower temperature so as to improve the image quality and stability of the processing solution.

In the present invention, each solution is usable for processing two or more photosensitive materials. For example, a color negative film and a color paper are processed with the same solution to reduce the cost of the processing machine and to simplify the process.

The silver halide photosensitive material for color photography of the present invention has a specified photographic sensitivity of preferably at least 320, more preferably 320 to 3200.

The term "specified photographic sensitivity" herein indicates a sensitivity according to ISO sensitivity of the International Standard. Detailed description is made from the right lower column, page (3) to the left upper column on page (6) of J. P. KOKAI No. Sho 63-226650. The reason why the sensitivity determination method which is not the same as the method for the determination of ISO is employed is as follows: in the determination of ISO sensitivity, it is necessary that the photosensitive material is developed by a process designated for each photosensitive material on the fifth day after the exposure.

The specified photographic sensitivity in the present invention is determined by a specified developing process (CN-16 process of Fuji Photo Film Co., Ltd.) a short time (0.5 to 6 hours) after the exposure.

At least one blue-sensitive layer, at least one green-sensitive layer and at least one red-sensitive layer each comprising a silver halide emulsion are formed on a support to form the photosensitive material of the present invention. The number of the silver halide emulsion layers and photo-insensitive layers is not particularly limited. A typical example of the silver halide photosensitive material comprises at least two color-sensitive layers (each comprising two or more silver halide emulsion layers having substantially the same color sensitivity but different degree of sensitivity) formed on the support. The photosensitive layer is a unit photosensitive layer sensitive to any of blue, green and red lights. In the multi-layered silver halide color photosensitive materials, the arrangement of the unit photosensitive layers is: a red-sensitive layer, a green-sensitive layer and a blue-sensitive layer in this order from the support. The whole hydrophilic colloid layers including these color-sensitive emulsion layers are calleld "photosensitive layer".

The preferred maximum spectral sensitivity wave length in each layer is, for example, as follows: 420 to 480 nm (blue-sensitive layer), 520 to 580 nm (green-sensitive layer) and 620 to 680 nm (red-sensitive layer).

A photoinsensitive layer such as an intermediate layer can be provided between the silver halide photosensitive layers or as the top layer or the bottom layer.

The intermediate layer may contain a coupler or DIR compound as described in J. P. KOKAI Nos. Sho 61-43748, 59-113438, 59-113440, 61-20037 and 61-20038, or an ordinary color-mixing inhibitor.

The two or more silver halide emulsion layers constituting the unit photosensitive layer have preferably a structure consisting of two layers, i.e. a high sensitivity emulsion layer and a low sensitivity emulsion layer, as described in West German Patent No. 1,121,470 or British Patent No. 923,045. Usually the arrangement of the layers is such that the sensitivity thereof decreases gradually toward the support. A photoinsensitive layer may be providedbetween the silver-halide emulsion layers. An emulsion layer having a low sensitivity may be formed away from the support and an emulsion layer having a high sensitivity may be formed close to the support as described in J. P. KOKAI Nos. Sho 57-112751, 62-200350, 62-206541 and 62-206543.

An example of the arrangement is a structure consisting of a blue-sensitive layer having a low sensitivity (BL)/blue-sensitive layer having a high sensitivity (BH)/green-sensitive layer having a high sensitivity (GH)/green sensitivive layer having a low sensitivity (GL)/red-sensitive layer having a high sensitivity (RH)/red-sensitive layer having a low sensitivity (RL); BH/BL/GL/GH/RH/RL; or BH/BL/GH/GL/RL/RH toward the support.

Another arrangement is that of three layers having sensitivities gradually lowered toward the support, i.e. a top layer (a silver halide emulsion layer having the highest sensitivity), middle layer (a silver halide emulsion layer having a lower sensitivity) and bottom layer (a silver halide emulsion layer having a sensitivity lower than that of the middle layer) as described in J. P. KOKOKU No. Sho 49-15495. Even in such an arrangement comprising three layers having sensitivities different from each other, a sensitive layer may further comprise an emulsion layer having a medium sensitivity/emulsion layer having a high sensitivity/emulsion layer having a low sensitivity in the order toward the support as described in J. P. KOKAI No. Sho 59-202464.

In another example, the arrangement may be as follows: high-sensitivity emulsion layer/low sensitivity emulsion layer/medium sensiitivity emulsion layer or low sensitivity emulsion layer/medium sensitivity emulsion layer/high sensitivity emulsion layer. When the photosensitive material has four or more layers, the arrangement of them may be varied as described above.

For improving the color reproducibility, it is preferred to form a donor layer (CL) having an interlayer effect and a spectral sensitivity distribution different from that of the main photosensitive layers such as BL, GL and RL at a position adjacent to or close to the main photosensitive layers as described in U.S. Pat. Nos. 4,663,271, 4,705,744 and 4,707,436 and J. P. KOKAI Nos. Sho 62-160448 and 63-89850.

Thus, the structure and arrangement of the layers can be selected depending on the use of the photosensitive material.

The detailed description will be made on an emulsion of the tabular silver halide grains used for the maximum red-sensitive layer in the present invention.

In the emulsion of the tabular silver halide grains used in the present invention, a term "aspect ratio" indicates the ratio of the diameter to the thickness of silver halide grains. The term "diameter" herein indicates the diameter of a circle having an area equal to the projection area of the grain in the observation of the silver halide emulsion with a microscope or electron microscope. Therefore, when the aspect ratio is at least 2, the diameter of the circle is at least twice as large as the thickness of the grain.

The diameter of the tabular silver halide grains in the silver halide emulsion of the present invention is at least twice as large as the thickness of the grain, preferably 3 to 20 times, more preferably 4 to 15 times and particularly preferably 5 to 10 times as large as the latter. The proportion of the area of the tabular silver halide grains is at least 50%, preferably at least 70% and particularly preferably at least 85%, based on the total projection area of the whole silver halide grains.

The diameter of the tabular silver halide grains is 0.02 to 20 $\mu$m, preferably 0.3 to 10.0 $\mu$m and particularly preferably 0.4 to 5.0 $\mu$m. The thickness of the grain is preferably 0.5 $\mu$m or below. The term "diameter" herein indicates the diameter of a circle having an area equal to the projection area of the grain. The thickness of the grain indicates the distance between the two parallel planes of the tabular silver halide grain.

The more preferred tabular silver halide grains in the present invention are those having a diameter of 0.3 to 10.0 $\mu$m, a thickness of 0.3 $\mu$m or below and an average ratio of the diameter to the thickness of 5 to 10. When the size of the grains is larger than these ranges, the photographic properties of the photosensitive material are impaired when it is folded, firmly rolled or brought in contact with something sharp. Still more preferred is a silver halide grain emulsion in which at least 85%, based on the total projection area of the whole silver halide grains, of the grains have a diameter of 0.4 to 5.0 $\mu$m and an average ratio of the diameter to the thickness of at least 5.

The tabular silver halide grains used in the present invention preferably comprise silver bromide, silver bromoiodide having a silver chloride content of 15 molar % or below, silver chlorobromoiodide having a silver chloride content of 50 molar % or below and silver iodide content of 2 molar % or below, or silver chlorobromide. In the composition comprising mixed silver halides, the silver halides may be distributed either uniformly or ununiformly.

The emulsion of the tabular silver halide grains used in the present invention is described in a report of Cugnac and Chatean, Duffin "EPhotographic Emulsion Chemistry" (published by Focal Press in New York in 1966), pages 66 to 72, and "Phot. Journal" 80 (1940) edited by A. P. H. Trivelli and W. F. Smith, page 285. The emulsion can be easily prepared by, for example, a method described in J. P. KOKAI Nos. Sho 58-113927, 58-113928 or 58-127921.

The tabular silver halide grains of the present invention can be chemically sensitized, if necessary. The chemical sensitization can be conducted by, for example, a method described on pages 675 to 735 of "Die Grundlagen der Photographischen Prozesse mit Silberhalogeniden" edited by H. Frieser (Akademische verlagsgesellschaft. 1968).

Namely, sensitization can be conducted by a sensitization method with a chalcogen-containing compound reactive with active gelatin or silver (selected from among thiosulfates, thioureas, mercapto compounds, rhodanines, selenoureas, phosphine selenides, phosphine tellurides, etc.); a reduction sensitization method with a reducing substance (selected from among stannous salts, amines, hydrazine derivatives, formamidinesulfinic acids, silane compounds, etc.); or a sensitization with a noble metal (selected from among gold complex salts, complex salts of the Group VIII metals of the Periodic Table such as Pt, Ir and Pd, etc.). These methods can be employed either singly or in combination of them.

The details of the chalcogen sensitization method are described in, for example, U.S. Pat. Nos. 1,574,944, 2,278,947, 2,410,689, 2,728,668 and 3,656,955. The reduction sensitization method is described in, for example, U.S. Pat. Nos. 2,419,974, 2,983,609 and 4,054,458. The noble metal sensitization method is described in, for example, U.S. Pat. Nos. 2,399,083 and 2,448,060 and British Patent No. 618,061.

From the viewpoint of saving silver, the tabular silver halide grains of the present invention are preferably sensitized with gold, the chalcogen-containing compound or a combination of them.

The tabular silver halide grains of the present invention can be spectrosensitized with a methine dye or the like, if necessary. In addition to the above-described improved sharpness, the tabular silver halide grains of the present invention have another characteristic feature, i.e. a high spectral speed. The dyes usable herein include cyanine dyes, merocyanine dyes, composite cyanine dyes, composite merocyanine dyes, holopolar cyanine dyes, hemicyanine dyes, styryl dyes and hemioxonol dyes. Particularly useful are cyanine dyes, merocyanine dyes and composite melocyanine dyes.

The sensitizing dyes usable herein are those described in, for example, German Patent No. 929,080, U.S. Pat. Nos. 2,493,748, 2,503,776, 2,519,001, 2,912,329, 3,656,959, 3,672,897 and 4,025,349, British Patent No. 1,242,588 and J. P. KOKOKU No. Sho 44-14030.

These sensitizing dyes are usable either singly or in combination of them. The combination of the sensitizing dyes is often used for the purpose of supersensitization. Typical examples of them are described in U.S. Pat. Nos. 2,688,545, 2,977,229, 3,397,060, 3,522,052, 3,527,641, 3,617,293, 3,628,964, 3,666,480, 3,672,898, 3,679,428, 3,814,609 and 4,026,707, British Patent No. 1,344,281, J. P. KOKOKU No. Sho 43-4936 and 53-12375, and J. P. KOKAI Nos. Sho 52-109925 and 52-110618.

The photographic emulsion used in the present invention may contain various compounds for the purpose of stabilizing the photographic properties or preventing the fogging in the course of the production of the photosensitive material, storage or photographic process. They include compounds known as antifoggant or stabilizer, for example, azoles such as benzothiazolium salts, nitroimidazoles, triazoles, benzotriazoles and benzoimidazoles (particularly nitro- or halogen-substituted compounds); heterocyclic mercapto compounds such as mercaptothiazoles, mercaptobenzothiazoles, mercaptobenzimidazoles, mercaptothiadiazoles, mercaptotetrazoles (particularly 1-phenyl-5-mercaptotetrazole) and mercaptopyrimidines; the above-described heterocyclic mercapto compounds which further have a water-soluble group such as carboxyl or sulfonic acid group; thioketo compounds such as oxazolinethion; azaindenes such as triazaindenes and tetrazaindenes [particularly 4-hydroxy-substituted (1,3,3a,7) tetrazaindenes]; benzenethiosulfonic acids; and benzenesulfinic acid. As for the detailed examples of them and method for using them, refer to. for example, U.S. Pat. Nos. 3,954,474, 3,982,947 and 4,021,248 and J. P. KOKOKU No. Sho 52-28660.

The above-described emulsion of the present invention is preferably a monodisperse emulsion.

The term "monodisperse emulsion" herein indicates an emulsion having such a grain diameter distribution that the coefficient of variation of the diameter of the silver halide grains is 0.25 or below. The term "coefficient of variation" herein indicates a value obtained by dividing the standard deviation of the grain diameter by the average grain diameter. Namely, when the grain diameter of each grains in the emulsion is given by "ri" and the number of them is "ni", the average grain diameter is given by the following formula:

Average particle size=$\Sigma rini/\Sigma ni$ and the standard deviation thereof is defined as follows:

Standard deviation=$\Sigma(ri-\bar{r})^2/\Sigma ni$ $\bar{r}$:Average particle size The term "diameter of each grain" indicates that the diameter corresponds to that of a projection area of the grain in the silver halide emulsion microphotographed by a method (usually electron microscopic photography) well known in the art as described in T. H. James et al. "The Theory of the Photographic Process", Edition 3, pages 36 to 43 (published by Macmillian Publishing Co., Inc. in 1966). This term for the silver halide grain is herein defined as the diameter of a circle having an area equal to that of the projection area of the silver halide grain as described in this book. Therefore, even when the shape of the silver halide grain is not globular (such as cubic, octahedral, tetradecahedral, tabular or potato-shaped), the average grain diameter "r" and the deviation "S" thereof can be determined as described above.

The coefficient of variation of the diameter of the silver halide grains is 0.25 or below, preferably 0.20 or below and more preferably 0.15 or below.

It is particularly preferred that the tabular silver halide emulsion of the present invention is an emulsion of monodisperse hexagonal tabular silver halide grains as described in J. P. KOKAI No. Sho 63-151618 and others.

The term "hexagonal tabular silver halide grain" herein indicates a grain characterized by having the hexagonal {1,1,1} face and an adjucent sides ratio of 2 or below. The term "adjucent sides ratio" herein indicates the ratio of the longest side to the shortest side of the hexagon. The corners of the hexagonal tabular silver halide grain of the present invention may be slightly rounded on condition that the adjucent sides ratio thereof is 2 or below. When the corners are rounded, the length of the sides is determined by extending the lines of the straight edges so that they intersect. The length of the side is given by the distance between two points of the intersection. At least ½, particularly at least ⅘ of each side of the hexagonal tabular grains of the present invention is substantially straight. The adjucent sides ratio is preferably 1 to 1.5 in the present invention.

The emulsion of the hexagonal tabular silver halide grains of the present invention comprises a dispersion medium and silver halide grains. At least 50%, preferably at least 70%, and more preferably at least 90%, of the projection area of the silver halide grains is occupied by the above-described hexagonal tabular silver halide grains.

The silver halide of the hexagonal tabular silver halide grains of the present invention may be any of silver bromide, silver bromoiodide, silver chlorobromide and silver chlorobromoiodide. Among them, preferred are silver bromide and silver bromoiodide. Silver iodide content of silver bromoiodide is 0 to 30 molar %, preferably 2 to 15 molar % and more preferably 4 to 12 molar %. As for the distribution of silver iodide in the grain, it may be uniformly dispersed in the whole grain; the silver iodide content in the core of the grain may be different from that in the surface layer thereof; or the grain may have two or more layers having different silver iodide contents to form a so-called multi-layer structure. Among them, preferred are grains of so-called internal iodine type wherein the silver iodide content in the grain surface is lower than that in the core.

The emulsion of the hexagonal tabular silver halide grain emulsion can be prepared by a method described in U.S. Pat. No. 4,797,354.

The method for the preparation of the emulsion of the hexagonal tabular silver halide grain is divided into steps of core formation, Ostwald ripening and growing of grains. In the core formation step, the core is formed while pBr is kept in the range of 1.0 to 2.5 under supersaturation conditions (including the temperature, gelatin concentration, addition rates of the aqueous silver salt solution and aqueous alkali halide solution, pBr, iodine ion content, stirring rotation rate, pH, quantity of solvent for silver halide, salt concentration, etc.) so as to form cores (tabular grain cores) having parallel twin planes in an as large as possible amount. In the Ostwald ripening step, the temperature, pBr, pH, gelatin concentration, quantity of solvent for silver halide, etc. are controlled so that grains other than the tabular grain cores formed in the core-formation step are eliminated to grow only the tabular grain cores, thereby obtaining cores having an excellent monodispersibility. By controlling pBr and the amounts of silver ion and the halogen ion to be added in the grain-growing step, the hexagonal tabular silver halide grains having a desired aspect ratio and grain size can be obtained. In the step of growing the grains, it is preferred to control the addition rate of silver ion and the halogen ion at 30 to 100% of the critical growing rate of the crystal.

In the emulsion of the present invention, it is preferred that 50% of the silver halide grains have at least 10 dislocations per grain.

The average grain dislocations can be observed by, for example, a direct method with a transmission electron microscope at a low temperature as described in J. F. Hamilton, Phot. Sci. Eng., 11, 57 (1967) and T. Shiozawa, J. Soc. Phot. Sci. Japan, 35, 213 (1972). In this method, the silver halide grain taken out from the emulsion so carefully that such a pressure as to cause the dislocation in the grain is not applied to the grain is placed on a mesh for the electron microscopic observation and then observed by the transmission method while the sample is cooled so as to prevent the damage (such as printout) caused by the electron beam. Since the thicker the grain, the more difficult the transmission of the electron beam, it is preferred to use a high-voltage (200 KV for 0.25 $\mu$m thick grain) electron microscope to make the observation clearer. From the photograph of the grain thus obtained, the position and number of the dislocations in the grain observed from a direction perpendicular to the main plane are known.

The site of the dislocation in the tabular grain of the present invention ranges from a point, which locates in the range of x % of the length from the center in the longitudinal direction of the grain to the side, to the side. "x" is preferably $10 \leq x < 100$, more preferably $30 \leq x < 98$ and most preferably $50 \leq x < 95$. The shape obtained by linking the starting points of the dislocation is similar to that of the grain, though it is sometimes deformed. The dislocation line runs from around the center toward the side and it is often a zigzag line.

As for the number of the dislocations in the tabular grain in the present invention, preferably at least 50% of the silver halide grains have at least 10 dislocations per grain, more preferably at least 80% of the grains have at least 10 dislocations per grain, and particularly at least 80% of the grains have at least 20 dislocations per grain.

In the preferred tabular silver halide grains at least 50% by weight of which has at least 10 dislocation lines per grain in the present invention, it is desirable that relative standard deviation of the silver iodide content of each silver halide grain is not more than 30%, particularly not more than 20%.

Silver iodide content of each grain in the emulsion can be determined by analyzing the composition of the grain with, for example, an X-ray microanalyzer. The term "relative standard deviation of silver iodide content of each grain" herein indicates a value obtained by determining silver iodide content of each of at least 100 grains in the emulsion with, for example, an X-ray microanalyzer, and calculating the value by the formula:(standard deviation of silver iodide content)/(average silver iodide content)×100. The concrete method for determining silver iodide content of each grain in the emulsion is described in, for example, European Patent No. 147,868 A.

When the relative standard deviation of silver iodide content of each grain is large, the appropriate points of the chemical sensitization of the respective grains are various to make the bringing out of the properties of all the grains impossible and, in addition, the relative standard deviation of the number of the dislocations among the grains is large.

There is a correlation in some cases between the silver iodide content Yi (molar %) and the diameter Xi (micron) corresponding to the globe in each grain. No correlation is desirable.

The structure of the halogen composition of the tabular grain can be confirmed by combining X-ray diffraction, EPMA (or XMA) method wherein the silver halide grain is scanned with electron beam to detect the silver halide composition and ESCA (or XPS) method wherein the grain is irradiated with X-rays and the photoelectrons coming out of the grain surface are spectroanalyzed.

The term "grain surface" herein indicates a part ranging from the surface to a depth of about 50 A. The halogen composition in this part can be usually determined by the ESCA method. The core of the grain indicates a part other than the surface part.

The emulsion of the tabular grains having the dislocation lines can be prepared by a method described in J. P. KOKAI Nos. Sho 63-220238 and Hei 2-310862. The range of the grain size distribution is preferably narrow in the silver halide emulsion of the present invention. A method described in Japanese Patent Application No. Sho 63-151618 which comprises core formation, Ostwald ripening and grain growing steps is preferably employed.

However, the emulsion easily became heterogeneous unless the silver iodide content of each grain in the emulsion was strictly controlled in the prior art.

For making the silver iodide content of each grain in the emulsion uniform, it is important to make the size and shape of the grains as uniform as possible after the completion of the Ostwald ripening. Further, an aqueous silver nitrate solution and an aqueous alkali halide solution are added by a double jet method while pAg is kept constant in the range of 6.0 to 10.0. To form a particularly uniform coating, the degree of supersaturation of the solution is preferably high in the course of the addition. It is desirable that the degree of supersaturation during the addition is relatively high so that the growing rate of the crystal is 30 to 100% of the critical crystal growth rate as described in, for example, U.S. Pat. No. 4,242,445.

The dislocation of the tabular grain of the present invention can be controlled by forming a special high-iodine phase in the grain. In particular, a tabular grain is prepared, a high iodine phase is formed around the grain and it is then covered with a phase having an iodine content lower than that of the high-iodine phase. To make the silver iodide content of the grains uniform, it is important to suitably select the high-iodine phase-forming conditions.

The term "internal high-iodine phase" indicates a solid solution of an iodine-containing silver halide. The silver halide in this case is preferably silver iodide, silver bromoiodide or silver chlorobromoiodide. Among them, silver iodide compound (iodine content: 10 to 40 molar %) is preferred and silver iodide is particularly preferred.

The internal high-iodine phase is not uniformly deposited on the plane surface of the tabular grain in the substrate but is locally dispersed thereon. The localized deposition may occur on any of the main planes, side faces, sides and corners. An internal high-iodine phase can be arranged selectively and epitaxially.

For this purpose, a so-called conversion method wherein an iodide salt is added singly or an epitaxial bonding method describedin, for example, J. P. KOKAI Nos. sho 59-133540, 58-108526 and 59-162540 can be employed. In such a case, it is effective in obtaining uniform silver iodide content of the respective grains to select the conditions as described below. The pAg in the step of the addition of the iodide salt is preferably in the range of 8.5 to 10.5, particularly preferably 9.0 to 10.5. The temperature is preferably kept in the range of 50 to 30° C. The iodide salt in an amount of at least 1 molar % based on the whole silver is added over a period of 30 seconds to 5 minutes under thorough stirring.

The iodine content of the tabular grains in the substrate is lower than that in the high-iodine phase. It is preferably 0 to 12 molar %, more preferably 0 to 10 molar %.

The iodine content of the outer phase covering the high-iodine phase is lower than that of the high-iodine phase. It is preferably 0 to 12 molar %, more preferably 0 to 10 molar % and most preferably 0 to 3 molar %.

The internal high-iodine phase is located within 5 to 80 molar % (in terms of silver, based on the whole grain) around the center of the major axis of the average grain. It is preferably located in a circular area around the center of the grain. More preferably, it is located in a circular area in the range of 10 to 70 molar %, particularly 20 to 60 molar % around the center.

The term "major axis direction" of the grain indicates a direction of the diameter of the tabular grain, and the term "minor axis direction" indicates the direction of the thickness of the grain.

The iodine content of the internal high-iodine phase is at least 5-times or particularly preferably at least 20-times higher than the average iodine content of silver iodide, silver bromoiodide or silver chlorobromoiodide contained in the surface of the grain.

The quantity of the silver halide forming the internal high-iodine phase is not larger than 50 molar %, preferably not larger than 10 molar % and particularly not larger than 5 molar %, based on the whole silver in the grain.

The properties of the silver halide grains can be controlled by conducting the step of forming the silver halide precipitate in the presence of various compounds. Such compounds may be fed into the reactor in the initial stage. They can be added also together with one or more salts by an ordinary method. Namely, the properties of the silver halide grains can be controlled by conducting the step of forming the silver halide precipitate in the presence of compounds of, for example, copper, iridium, lead, bismuth, cadmium, zinc (such as chalcogen compounds of sulfur, selenium and tellurium), gold and the group VII noble metals as described in U.S. Pat. Nos. 2,448,060, 2,628,167, 3,737,313 and 3,772,031, and Research Disclosure, Vol. 134, 13452 (June, 1975). The inside of the grain can be reduction-sensitized in the step of forming the precipitate in the silver halide emulsion as described in J. P. KOKOKU No. Sho 58-1410 and Moisar et al., Journal of Photographic Science, Vol. 25 (1977), pages 19 to 27.

In the tabular grains used in the present invention, silver halides having compositions different from each other may be bonded together by an epitaxial bond and, in addition, they may be bonded with a compound other than the silver halides such as silver rhodanide or lead oxide. Such grains in the emulsion are disclosed in, for example, U.S. Pat. Nos. 4,094,684, 4,142,900 and 4,459,353, British Patent No. 2,038,792, U.S. Pat. Nos. 4,349,622, 4,395,478, 4,433,501, 4,463,087, 3,656,962 and 3,852,067 and J. P. Kokai No. Sho 59-162540.

The tabular silver halide emulsion of the present invention is usually chemically sensitized.

The chemical sensitization is conducted after the formation of the silver halide emulsion. The emulsion may be washed with water in the course of the chemical sensitization after the formation of the emulsion.

The chemical sensitization can be conducted at pAg 5 to 10, pH 5 to 8 and 30~80° C. with sulfur, selenium, tellurium, gold, platinum, palladium or iridium sensitizer or a combination of two or more of them as described in Research Disclosure No. 17643 (December, 1978; page 23) and No. 18716 (November, 1979; right column on page 648).

The emulsion of the tabular silver halide grains of the present invention is sensitized preferably in the presence of a spectral sensitizing dye. The method for the chemical sensitization in the presence of the spectral sensitizing dye is described in, for example, U.S. Pat. Nos. 4,425,426 and 4,442,201 and J. P. KOKAI Nos. Sho 59-9658, 61-103149 and 61-133941. The spectral sensitizing dye to be used herein may be any of those usually used for silver halide photosensitive materials. They are described in Research Disclosure No. 17643 (pages 23 and 24) and No. 18716 (from the right column, page 648 to the right column, page 649). The spectral sensitizing dyes may be used either singly or in the form of a mixture of two or more of them.

The spectral sensitizing dye can be added before the chemical sensitization (during the formation of the grains, after the formation thereof or after washing with water), in the course of the chemical sensitization or after the chemical sensitization. It is added preferably after the formation of the grains and before the chemical sensitization or after the completion of the chemical sensitization.

Although the amount of the spectral sensitizing dye to be added is not particularly limited, it is preferably 30 to 100%, more preferably 50 to 90%, based on the amount of the saturation adsorption.

The emulsion of the tabular silver halide grains of the present invention is usually spectrally sensitized. The spectral sensitizing dyes used are described in the above-described two books of Research Disclosure. A spectral sensitizing dye which may be the same or different from that contained in the emulsion at the time of the chemical sensitization may be supplemented to the emulsion for the spectral sensitization, if necessary.

The emulsions of the present invention may be used singly or in combination of two or more emulsions having different grain sizes for forming the photosensitive emulsion layer. When two or more emulsions are used, they are preferably used in the form of a mixture of them for forming a layer, though they may be used separately for forming the layers. When two or more emulsions are used, they may be a combination of an emulsion having an average aspect ratio specified in the present invention with another emulsion. The use of the mixture of the emulsions as described above is preferred from the viewpoints of the gradation control, graininess control in all the area ranging from a low exposure area to a high exposure area, and color development dependency (time and components of the developer such as color developing agent and sodium sulfite and pH) control.

It is particularly preferred that the emulsion of the present invention has a relative standard deviation of the silver iodide content among the grains of not higher than 20%. The relative standard devition is described in J. P. KOKAI Nos. Sho 60-143332 and 60-254032.

The term "thickness of emulsion layer" herein indicates the thickness of the layer determined at 25° C. under control of humidity (55% for two days). The thickness can be determined with a commercially available film thickness gauge. Although the effect of the present invention becomes larger as the total thickness of the hydrophilic colloidal layers on the emulsion layer-side is reduced, the reduction in the thickness is limited by the volume of the binder such as gelatin, coupler and dispersing medium. The film thickness is thus preferably 10 to 22 $\mu$m, more preferably 12 to 20 $\mu$m and particularly preferably 15 to 18 $\mu$m.

The rate of swelling of the color photographic photosensitive material of the present invention in the developer is preferably at least 2.3 from the viewpoint of the rapid diffusion of the developing agent. It is more preferably 2.4 to 4 and particularly 2.4 to 3. When it is excessively high, the diffusion distance is prolonged to make the development slow.

The term "rate of swelling" herein indicates a value obtained by dividing the thickness of the film swollen in the developer (thickness of the photographic layers on the photosensitive layer side and the support) by the thickness of the dry film.

The thickness of the film swollen in the developer can be determined by a method described in A. Green and G. I. P. Levenso, J. Phot. sci., 20, 205 (1972). Namely, it can be known from the equilibrium thickness of the film swollen in the developer kept at 38° C. The formulation of the developer is, for example, that described in Examples given below.

In the determination of the rate of swelling as defined in the present invention, developer A is used.

The two-equivalent coupler in the red-sensitive layer used in the present invention may be a known one. In particular, a two-equivalent coupler selected from among the couplers described below is usable.

The two-equivalent coupler forms one molecule of a dye when it forms two atoms of image silver in the color development. In an ordinary four-equivalent coupler, four silver halides are reduced and one molecule of the dye is formed. However, in the two-equivalent coupler, two silver halides are reduced and one molecule of the dye is formed. Therefore, for obtaining a color image by using the two-equivalent coupler, the amount of the silver halide is only a half of that necessitated when the four-equivalent coupler is used.

In the present invention, the coloring velocity in the red-sensitive layer can be increased by using such a two-equivalent coupler in an amount of at least 50 molar %, preferably at least 75 molar %, based on the total couplers in the red-sensitive layer.

The two-equivalent cyan couplers used in the present invention include phenol and naphthol couplers. Preferred are two-equivalent couplers described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Disclosure No. 3,329,729, European Patent Nos. 121,365A and 249,453A, U.S. Pat. Nos. 3,446,622, 4,333,999, 4,775,616, 4,451,559, 4,427,767, 4,690,889, 4,254,212 and 4,296,199 and J. P. KOKAI No. Sho 61-42658. Further, pyrazoloazole couplers described in J. P. KOKAI Nos. Sho 64-553, 64-554, 64-555 and 64-556 and imidazole couplers described in U.S. Pat. No. 4,818,672 are also usable. Particularly preferred are two-equivalent naphthol couplers of oxygen-linked coupling-off type described. in U.S. Pat. Nos. 4,052,212, 4,146,396, 4,228,233 and 4,296,200.

The preferred silver halide to be contained in the photographic emulsion layer of the photographic photosensitive material used in the present invention is silver bromoiodide, silver chloroiodide or silver chlorobromoiodide containing less than about 30 molar % of silver iodide. Particulrly preferred is silver bromoiodide or silver chlorobromoiodide containing about 2 to 10 molr % of silver iodide.

The silver halide grains in the photographic emulsion may be in a regular crystal form such as a cubic, octahedral or tetradecahedral form; an irregular crystal form such as spherical or tabular form; or a complex crystal form thereof. They include also those having a crystal fault such as a twin plate.

The silver halide grain diameter may range from about 0.2 $\mu$m or less to as large as that having a projection area diameter of about 10 $\mu$m. The emulsion may be either a polydisperse emulsion or monodisperse emulsion.

The silver halide photographic emulsion usable in the present invention can be prepared by processes described in, for example, Research Disclosure (RD), No. 17643 (December, 1978), pp. 22 to 23, "1. Emulsion preparation and types"; RD No. 18716 (November, 1979), p. 648; RD No. 307105 (November, 1989), pp. 863 to 865; P. Glafkides, Chemie et Phisique Photographique, Paul Montel, 1967; G. F. Duffin, Photographic Emulsion Chemistry (Focal Press, 1966); V. L. Zelikman et al., Making and Coating Photographic Emulsion (Focal Press, 1964).

Monodisperse emulsions described in U.S. Pat. Nos. 3,574,628 and 3,655,394 and British Patent No. 1,413,748 are also preferred.

The crystal structure of the grains in the above emulsion may be uniform; the grains may comprise an inside portion and an outside portion which are composed of silver halides different from each other; or the structure may be a laminated one. Different silver halide grains can be bonded together by an epitaxial bond or they can be bonded with a compound other than silver halides such as silver rhodanate or lead oxide. A mixture of grains having various crystal forms can also be used.

The emulsion may be of a surface-latent image type for forming a latent image mainly on the surface thereof, of an internal latent image type for forming a latent image in the grains or of such a type that a latent image is formed both on the surface and in the grains. The emulsion must be of a negative type. In the internal latent image type emulsions, a core/shell type internal latent image type emulsion described in J.P. KOKAI No. Sho 63-264740 may also be used. Processes for producing the core/shell type internal latent image type emulsion are described in J.P. KOKAI No. Sho 59-133542. The thickness of the shells in the emulsion which varies depending on the developing process is preferably 3 to 40 nm, particularly preferably 5 to 20 nm.

The silver halide emulsion to be used in the present invention is usually physically and chemically ripened and spectrally sensitized. The additives to be used in these steps are shown in Research Disclosure Nos. 17643, 18716 and 307105. The portions in which the additives are mentioned in these three books of Research Disclosure are summarized in a table given below.

A mixture of two or more photosensitive silver halide emulsions different from one another in at least one of the grain size, grain size distribution, halogen composition, shape of the grains and sensitivity can be used for forming a layer.

Silver halide grains having the fogged surface described in U.S. Pat. No. 4,082,553, silver halide grains having fogged core and colloidal silver described in U.S. Pat. No. 4,626,498 and J.P. KOKAI No. Sho 59-214852 can be preferably used for forming the photosensitive silver halide emulsion layer and/or substantially photo-insensitive, hydrophilic colloid layer. The term "emulsion of silver halide grains having fogged core or surface" indicates an emulsion of silver halide grains which can be subjected to uniform (non-imagewise) development irrespective of exposed or non-exposed parts of the photosensitive material. Processes for producing the silver halide grains having the fogged core or surface are described in U.S. Pat. No. 4,626,498 and J. P. KOKAI No. 59-214852.

The silver halide for forming the core of the core/shell type silver halide grains having the fogged core may have the same or different halogen composition. The silver halides having the fogged core or surface include silver chloride, silver chlorobromide, silver bromoiodide and silver chlorobromoiodide. Although the size of the fogged silver halide grains is not particularly limited, the average grain size thereof is preferably 0.01 to 0.75 $\mu$m, particularly 0.05 to 0.6 $\mu$m. The shape of the grains is not particularly limited. The grains may be regular or in the form of a polydisperse emulsion. The dispersion is preferably of monodisperse system wherein at least 95% (by weight or by number of the grains) of the silver halide grains have a grain diameter within the average grain diameter±40%.

Fine grains of a photo-insensitive silver halide are preferably used in the present invention. The term "fine grains of photoinsensitive silver halide" indicates fine silver halide grains which are not sensitized in the image-forming exposure for forming a dye image and which are substantially not developed in the developing process. They are preferably previously not fogged.

The fine silver halide grains have a silver bromide content of 0 to 100 molar %. If necessary, they may contain silver chloride and/or silver iodide. They preferably contain 0.5 to 10 molar % of silver iodide.

The fine silver halide grains have an average grain diameter (average diameter of a projected area) of preferably 0.01 to 0.5 $\mu$m more preferably 0.02 to 2 $\mu$m.

The fine silver halide grains can be prepared by the same processes as those for the productin of ordinary photosensitive silver halides. In this case, it is unnecessary to chemically sensitize or spectrally sensitize the surface of the silver halide grains. It is preferred, however, to incorporate a known stabilizer such as a triazole, azaindene, benzothiazolium or mercapto compound or a zinc compound thereinto prior to the incorporation thereof into a coating solution. Colloidal silica can be preferably incorporated into the fine silver halide grain-containing layer.

The amount of silver to be applied to the photosensitive material of the present invention is preferably not larger than 8.0 $g/m^2$, most preferably not larger than 6.0 $g/m^2$. It is preferably not smaller than 0.3 $g/m^2$. When the photosensitive material is a photographic color photosensitive material, the amount of silver to be applied is not smaller than 2 $g/m^2$.

Known photographic additives usable in the present invention are also mentioned in the above-described three books of Research Disclosure, and the corresponding portions are shown in the following table.

| Additive | RD 17643 | RD 18716 | RD 307105 |
|---|---|---|---|
| 1. Chemical sensitizer | p. 23 | p. 648, right column | p. 866 |
| 2. Sensitivity improver | | p. 648, right column | |
| 3. Spectral sensitizer and supersensitizer | pp. 23 to 24 | p. 648, right column to p. 649, right column | pp. 866 to 868 |
| 4. Brightening agent | p. 24 | p. 647, right column | p. 868 |
| 5. Antifoggant and stabilizer | pp. 24 and 25 | p. 649, right column | pp. 868 to 870 |
| 6. Light absorber, filter, dye and UV absorber | pp. 25 to 26 | p. 649, right column to p. 650, left column | p. 873 |
| 7. Antistaining agent | p. 25, right column | p. 650, left and right columns | p. 872 |
| 8. Dye image stabilizer | p. 25 | p. 650, left column | " |
| 9. Hardener | p. 26 | p. 651, left column | pp. 874 to 875 |
| 10. Binder | " | p.651, left column | pp. 873 to 874 |
| 11. Plasticizer and lubricant | p. 27 | p. 650, right column | p. 876 |
| 12. Coating aid and surfactant | pp. 26 and 27 | p. 650, right column | pp. 875 to 876 |
| 13. Antistatic agent | p. 27 | p. 650, right column | pp. 876 to 877 |
| 14. Matting agent | | p. 650, right column | pp. 878 to 879 |

To prevent the deterioration of the photographic properties by gaseous formaldehyde, it is preferred to add to the photosensitive material a compound capable of reacting with formaldehyde to fix it as described in U.S. Pat. Nos. 4,411,987 and 4,435,503.

It is preferred to incorporate a mercapto compound described in U.S. Pat. Nos. 4,740,454 and 4,788,132, J.P. KOKAI Nos. Sho 62-18539 and Hei 1-283551 into the photosensitive material of the present invention.

It is also preferred to incorporate a compound which releases a fogging agent, development accelerator, solvent for the silver halides or a precursor thereof into the photosensitive material of the present invention irrespective of the amount of the developing silver formed by the development which is described in J.P. KOKAI No. Hei 1-106052.

It is also preferred to incorporate a dye dispersed by a process described in International Publication No. WO 88/04794 and J.P. KOKAI No. Hei 1-502912 or a dye described in EP 317,308A, U.S. Pat. No. 4,420,555 and J.P. KOKAI No. Hei 1-259358.

Various color couplers can be used in the present invention. Examples of them are given in patents described in the above-described Research Disclosure No. 17643, VII-C to G and No. 307105, VII-C to G.

Preferred yellow couplers are those described in, for example, U.S. Pat. Nos. 3,933,501, 4,022,620, 4,326,024, 4,401,752 and 4,248,961, J.P. KOKOKU No. Sho 58-10739, British Patent Nos. 1,425,020 and 1,476,760, U.S. Pat. Nos. 3,973,968, 4,314,023 and 4,511,649, and European Patent No. 249,473A.

Preferred magenta couplers are 5-pyrazolone and pyrazoloazole compounds. Particularly preferred are those described in U.S. Pat. Nos. 4,310,619 and 4,351,897, European Patent No. 73,636, U.S. Pat. Nos. 3,061,432 and 3,725,067, Research Disclosure No. 24220 (June, 1984), J.P. KOKAI No. Sho 60-33552, Research Disclosure No. 24230 (June, 1984), J.P. KOKAI Nos. Sho 60-43659, 61-72238, 60-35730, 55-118034 and 60-185951, U.S. Pat. Nos. 4,500, 630, 4,540,654 and 4,556,630, and International Publication No. WO 88/04795.

The four-equivalent cyan couplers usable in the present invention are phenolic and naphtholic couplers. Particularly preferred are those described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Unexamined Published Application No. 3,329,729, European Patent Nos. 121,365A and 249,453A, U.S. Pat. Nos. 3,446,622, 4,333,999, 4,775, 616, 4,451,559, 4,427,767, 4,690,889, 4,254,212 and 4,296, 199, and J.P. KOKAI No. Sho 61-42658. Further, pyrazoloazole couplers described in J.P. KOKAI Nos. Sho 64-553, 64-554, 64-555 and 64-556 and imidazole couplers described in U.S. Pat. No. 4,818,672 are also usable.

Typical examples of the polymerized color-forming couplers are described in, for example, U.S. Pat. Nos. 3,451, 820, 4,080,211, 4,367,282, 4,409,320 and 4,576,910, British Patent No. 2,102,137 and European Patent No. 341,188A.

The couplers capable of forming a colored dye having a suitable diffusibility are preferably those described in U.S. Pat. No. 4,366,237, British Patent No. 2,125,570, European Patent No. 96,570 and West German Patent (Publication) No. 3,234,533.

Colored couplers used for compensation for unnecessary absorption of the colored dye are preferably those described in Research Disclosure No. 17643, VII-G and No. 307105, VII-G, U.S. Pat. No. 4,163,670, J.P, KOKOKU No. Sho 57-39413, U.S. Pat. Nos. 4,004,929 and 4,138,258 and British Patent No. 1,146,368. Other couplers preferably used herein include couplers capable of compensating for an unnecessary absorption of the colored dye with a fluorescent dye released during the coupling as described in U.S. Pat. No. 4,774,181 and couplers having, as a removable group, a dye precursor group capable of forming a dye by reacting with a developing agent as described in U.S. Pat. No. 4,777,120.

Further, compounds which release a photographically useful residue during a coupling reaction are also preferably usable in the present invention. DIR couplers which release a development inhibitor are preferably those described in the patents shown in the above described RD 17643, VII-F and No. 307105, VII-F as well as those descried in J.P. KOKAI Nos. Sho 57-151944, 57-154234, 60-184248, 63-37346 and 63-37350 and U.S. Pat. Nos. 4,248,962 and 4,782,012.

The couplers which release a nucleating agent or a development accelerator in the image-form in the development step are preferably those described in British Patent Nos. 2,097,140 and 2,131,188 and J.P. KOKAI Nos. Sho 59-157638 and Sho 59-170840. Further, compounds capable of releasing a fogging agent, development accelerator, solvent for silver halides, etc. upon the oxidation-reduction reaction with an oxidate of a developing agent as described in J.P. KOKAI Nos. Sho 60-107029, Sho 60-252340, Hei 1-44940 and Hei 1-45687 are also preferred.

Other compounds usable for the photosensitive material according to the present invention include competing couplers described in U.S. Pat. No. 4,130,427, polyequivalent couplers described in U.S. Pat. Nos. 4,283,472, 4,338,393 and 4,310,618, DIR redox compound-releasing couplers, DIR coupler-releasing couplers, DIR coupler-releasing redox compounds and DIR redox-releasing redox compounds described in J.P. KOKAI Nos. Sho 60-185950 and 62-24252, couplers which release a dye that restores the color after coupling-off as described in European Patent Nos. 173,302 A and 313,308 A, ligand-releasing couplers described in U.S. Pat. No. 4,555,477, leuco dye-releasing couplers described in J.P. KOKAI No. Sho 63-75747 and fluorescent dye-releasing couplers described in U.S. Pat. No. 4,774,181.

The couplers used in the present invention can be incorporated into the photosensitive material by various known dispersion methods.

High-boiling solvents used for an oil-in-water dispersion method are described in, for example, U.S. Pat. No. 2,322, 027. The high-boiling organic solvents having a boiling point under atmospheric pressure of at least 175° C. and usable in the oil-in-water dispersio n method include, for example, phthalates [such as dibutyl phthalate, dicyclohexyl phthalate, di-2-ethylhexyl phthalate, decyl phthalate, bis(2, 4-di-t-amylphenyl) phthalate, bis(2,4-di-t-amylphenyl) isophthalate and bis(1,1-diethylpropyl) phthalate], phosphates and phosphonates [such as triphenyl phosphate, tricresyl phosphate, 2-ethylhexyldihenyl phosphate, tricyclohexyl phosphate, tri-2-ethylhexyl phosphate, tridodecyl phoshate, tributoxyethyl phosphate, trichloropropyl phosphate and di-2-ethylhexylphenyl phosphonate], benzoates [such as 2-ethylhexyl benzoate, dodecyl benzoate and 2-ethylhexyl-p-hydroxybenzoate], amides [such as N,N-diethyldodecaneamide, N,N-diethyllaurylamide and N-tetradecylpyrrolidone], alcohols and phenols [such as isostearyl alcohol and 2,4-di-tert-amylphenol], aliphatic carboxylates [such as bis(2-ethylhexyl) sebacate, dioctyl azelate, glycerol tributyrate, isostearyl lactate and trioctyl citrate], aniline derivatives [such as N,N-dibutyl-2-butoxy-5-tert-octylaniline] and hydrocarbons [such as paraffin, dodecylbenzene and diisopropylnaphthalenel]. Co-solvents usable in the present invention include, for example, organic solvents having a boiling point of at least about 30° C., preferably 50 to about 160° C. Typical examples of them include ethyl acetate, butyl acetate, ethyl propionate, methyl ethyl ketone, cyclohexanone, 2-ethoxyethyl acetate and dimethylformamide.

The steps and effects of the latex dispersion method and examples of the latices usable for the impregnation are described in, for example, U.S. Pat. No. 4,199,363 and West German Patent Application (OLS) Nos. 2,541,274 and 2,541,230.

The color photosensitive material used in the present invention preferably contains phenethyl alcohol or an antiseptic or mold-proofing agent described in J.P. KOKAI Nos. Sho 63-257747, Sho 62-272248 and Hei 1-80941 such as 1,2-benzoisothiazoline-3-on, n-butyl p-hydroxybenzoate, phenol, 4-chloro-3,5-dimethylphenol, 2-phenoxyethanol or 2-(4-thiazolyl) benzimidazole.

Suitable supports usable in the present invention are described, for example, on page 28 of the above-described RD. No. 17643; from right column, page 647 to left column, page 648 of RD. No. 18716; and on page 879 of RD. No. 307105. Preferred supports are, for example, triacetate supports (TAC) and polyester supports.

The film-swelling rate $T_{1/2}$ of the total hydrophilic colloidal layers on the emulsion layer-side of the photosensitive material of the present invention is preferably 30 seconds or below, more preferably 20 seconds or below. The film thickness is determined at 25° C. and at a relative humidity of 55% (2 days). The film-swelling rate $T_{1/2}$ can be determined by a method known in this technical field. For example, it can be determined with a swellometer described on pages 124 to 129 of A. Green et al., "Photogr. Sci. Eng.", Vol. 19, No. 2. $T_{1/2}$ is defined to be the time required for attaining the thickness of a half (½) of the saturated film thickness (the saturated film thickness being 90% of the maximum thickness of the film swollen with the color developer at 30° C. for 3 minutes and 15 seconds).

The film-swelling rate $T_{1/2}$ can be controlled by adding a hardener to gelatin used as the binder or by varying the time conditions after the coating.

The photosensitive material of the present invention preferably has a hydrophilic colloid layer (in other words, back layer) having a total thickness of 2 to 20 μm on dry basis on the opposite side to th e emulsion layer. The back layer preferably contains the above-described light absorber, filter dye, ultraviolet absorber, antistatic agent, hardener, binder, plasticizer, lubricant, coating aid, surfactant, etc. The swelling rate of the back layer is preferably 2.5 to 6.0.

The effect of the silver halide color photographic photosensitive material of the present invention is remarkable when the material is used for the production of a film unit provided with a lens as described in J. P. KOKOKU Nos. Hei 2-32615 and Japanese Utility Model Publication for Opposition Purpose No. Hei 3-39784.

The following Examples will further illustrate the present invention, which by no means limit the invention.

EXAMPLE 1

Preparation of multi-layer color photosensitive material:

A multilayer color photosensitive material, which will be referred to as "sample 101", was prepared by forming layers of the following compositions:

(Compositions of photosensitive layers)

Main materials to be used for forming the layers are classified as follows:

ExC: cyan coupler

ExM: magenta coupler

ExY: yellow coupler

ExS: sensitizing dye

UV: ultraviolet absorber

HBS: high-boiling organic solvent

H: gelatin hardener

The numerals for the respective components indicate the amount of coating given by g/m². Those for silver halides are given in terms of silver. Those for sensitizing dyes are given in terms of molar unit per mol of the silver halide contained in the same layer. (Sample 101)

The first layer (antihalation layer):

| | | |
|---|---|---|
| black colloidal silver | silver | 0.18 |
| glatin | | 1.60 |
| ExM-1 | | 0.11 |
| ExF-1 | | $3.4 \times 10^{-3}$ |
| ExF-2 (solid dispersed dye) | | 0.03 |
| ExF-3 (solid dispersed dye) | | 0.04 |
| HBS-1 | | 0.16 |

The second layer (intermediate layer):

| | | |
|---|---|---|
| ExC-2 | | 0.055 |
| UV-1 | | 0.011 |
| UV-2 | | 0.030 |
| UV-3 | | 0.053 |
| HBS-1 | | 0.05 |
| HBS-2 | | 0.02 |
| polyethyl acrylate latex | | $8.1 \times 10^{-2}$ |
| gelatin | | 1.75 |

The third layer (low-speed red-sensitive emulsion layer)

| | | |
|---|---|---|
| silver bromoiodide emulsion A | silver | 0.46 |
| ExS-1 | | $5.0 \times 10^{-4}$ |
| ExS-2 | | $1.8 \times 10^{-5}$ |
| ExS-3 | | $5.0 \times 10^{-4}$ |
| ExC-1 | | 0.16 |
| ExC-3 | | 0.045 |
| ExC-5 | | 0.0050 |
| ExC-7 | | 0.001 |
| ExC-8 | | 0.010 |
| Cpd-2 | | 0.005 |
| HBS-1 | | 0.090 |
| gelatin | | 0.87 |

The fourth layer (medium-speed red-sensitive emulsion layer)

| | | |
|---|---|---|
| silver bromoiodide emulsion D | silver | 0.70 |
| ExS-1 | | $3.0 \times 10^{-4}$ |
| ExS-2 | | $1.2 \times 10^{-5}$ |
| ExS-3 | | $4.0 \times 10^{-4}$ |
| ExC-1 | | 0.22 |
| ExC-2 | | 0.055 |
| ExC-5 | | 0.007 |
| ExC-8 | | 0.009 |
| Cpd-2 | | 0.036 |
| HBS-1 | | 0.11 |
| gelatin | | 0.70 |

The fifth layer (high-speed red-sensitive emulsion layer)

| | | |
|---|---|---|
| silver bromoiodide emulsion E | silver | 1.62 |
| ExS-1 | | $2.0 \times 10^{-4}$ |
| ExS-2 | | $1.0 \times 10^{-5}$ |
| ExS-3 | | $3.0 \times 10^{-4}$ |
| ExC-1 | | 0.133 |
| ExC-3 | | 0.040 |
| ExC-6 | | 0.040 |
| ExC-8 | | 0.014 |
| Cpd-2 | | 0.050 |
| HBS-1 | | 0.22 |
| HBS-2 | | 0.10 |
| gelatin | | 0.85 |

The sixth layer (intermediate layer)

| | | |
|---|---|---|
| Cpd-1 | | 0.07 |
| ExF-4 | | 0.03 |
| HBS-1 | | 0.04 |
| polyethyl acrylate latex | | 0.19 |
| gelatin | | 2.30 |

The seventh layer (low-speed green-sensitive emulsion layer)

| | | |
|---|---|---|
| silver bromoiodide emulsion A | silver | 0.24 |
| silver bromoiodide emulsion B | silver | 0.10 |
| silver bromoiodide emulsion C | silver | 0.14 |
| ExS-4 | | $4.0 \times 10^{-5}$ |
| ExS-5 | | $1.8 \times 10^{-4}$ |
| ExS-6 | | $6.5 \times 10^{-4}$ |
| ExM-1 | | 0.005 |
| ExM-2 | | 0.30 |
| ExM-3 | | 0.09 |
| ExY-1 | | 0.015 |
| HBS-1 | | 0.26 |

-continued

| | |
|---|---|
| HBS-3 | 0.006 |
| gelatin | 0.80 |
| The eighth layer (medium-speed green-sensitive emulsion layer) | |
| silver bromoiodide emulsion D     silver | 0.94 |
| ExS-4 | $2.0 \times 10^{-5}$ |
| ExS-5 | $1.4 \times 10^{-4}$ |
| ExS-6 | $5.4 \times 10^{-4}$ |
| ExM-2 | 0.16 |
| ExM-3 | 0.045 |
| EXY-1 | 0.008 |
| ExY-5 | 0.030 |
| HBS-1 | 0.14 |
| HBS-3 | $8.0 \times 10^{-3}$ |
| gelatin | 0.90 |
| The ninth layer (high-speed green-sensitive emulsion layer) | |
| silver bromoiodide emulsion E     silver | 1.29 |
| ExS-4 | $3.7 \times 10^{-5}$ |
| ExS-5 | $8.1 \times 10^{-5}$ |
| ExS-6 | $3.2 \times 10^{-4}$ |
| ExC-4 | 0.011 |
| ExM-1 | 0.016 |
| ExM-4 | 0.046 |
| ExM-5 | 0.023 |
| Cpd-3 | 0.050 |
| HBS-1 | 0.20 |
| HBS-2 | 0.08 |
| polyethyl acrylate latex | 0.26 |
| gelatin | 0.82 |
| The tenth layer (yellow filter layer) | |

-continued

| | |
|---|---|
| yellow colloidal silver     silver | 0.010 |
| Cpd-1 | 0.10 |
| ExF-5 (solid dispersed dye) | 0.06 |
| ExF-6 (solid dispersed dye) | 0.06 |
| ExF-7 (oil-soluble dye) | 0.005 |
| HBS-1 | 0.055 |
| gelatin | 0.70 |
| The eleventh layer (low-speed blue-sensitive emulsion layer) | |
| silver bromoiodide emulsion A     silver | 0.25 |
| silver bromoiodide emulsion C     silver | 0.25 |
| silver bromoiodide emulsion D     silver | 0.10 |
| ExS-7 | $8.0 \times 10^{-4}$ |
| ExY-1 | 0.010 |
| ExY-2 | 0.70 |
| ExY-3 | 0.055 |
| ExY-4 | 0.006 |
| ExY-6 | 0.075 |
| ExC-7 | 0.040 |
| HBS-1 | 0.25 |
| gelatin | 1.60 |
| The twelfth layer (high-speed blue-sensitive emulsion layer) | |
| silver bromoiodide emulsion F     silver | 1.30 |
| ExS-7 | $3.0 \times 10^{-4}$ |

-continued

| | |
|---|---|
| ExY-2 | 0.15 |
| ExY-3 | 0.06 |
| HBS-1 | 0.070 |
| gelatin | 1.13 |
| The thirteenth layer (the first protective layer) | |
| UV-2 | 0.08 |
| UV-3 | 0.11 |
| UV-4 | 0.26 |
| HBS-1 | 0.09 |
| gelatin | 1.20 |
| The fourteenth layer (the second protective layer) | |
| silver bromoiodide emulsion G     silver | 0.10 |
| H-1 | 0.30 |
| B-1 (diameter: 1.7 μm) | $5.0 \times 10^{-2}$ |
| B-2 (diameter: 1.7 μm) | 0.10 |
| B-3 | 0.10 |
| S-1 | 0.20 |
| gelatin | 1.75 |

Further, the respective layers suitably contain W-1 to W-3, B-4 to B-6, F-1 to F-17, iron salts, lead salts, gold salts, platinum salts, iridium salts, palladium salts and rhodium-salts in order to improve the storability, processability, pressure resistance, mildew-proofing and bacteria-proofing properties, antistatic properties and coating easiness.

TABLE 1

| Emulsion | Average AgI content (%) | Average grain diameter (μm) | Coefficient of variation of grain diameter (%) | Percentage of grains having diameter/thickness ratio of at least 2 (%) | Grain structure/shape |
|---|---|---|---|---|---|
| A | 2.1 | 0.55 | 25 | 81 | homogeneous structure, tabular |
| B | 9.1 | 0.63 | 26 | 84 | triple structure, tabular |
| C | 3.1 | 0.60 | 24 | 98 | triple structure, tabular |
| D | 4.2 | 0.80 | 19 | 92 | triple structure, tabular |
| E | 3.2 | 1.10 | 17 | 96 | triple structure, tabular |
| F | 10.8 | 1.75 | 27 | 60 | double structure, tabular |
| G | 1 | 0.07 | 15 | 0 | homogeneous structure, cubic |

In Table 1:
(1) The emulsions A to F were reduction-sensitized with thiourea dioxide and thiosulfonic acid in the step of preparation of the grains as described in an Example of J.P. KOKAI No. Hei 2-191938.
(2) The emulsions A to F were sensitized by gold sensitization, sulfur sensitization and selenium sensitization methods in the presence of a spectral sensitizing dye mentioned above for each photosensitive layer and sodium thiocyanate as described in an Example of J.P. KOKAI No. Hei 3-237450.
(3) In the preparation of tabular grains, a low-molecular weight gelatin was used as described in an Example of J.P. KOKAI No. Hei 1-158426.
(4) Dislocation lines as described in J.P. KOKAI No. Hei 3-237450 are obserbed on the tabular grains with a high-voltage electron microscope.

Preparation of dispersion of organic solid disperse dye:
ExF-2 which will be described below was dispersed as follows: 21.7 ml of water, 3 ml of 5% aqueous solution of sodium p-octylphenoxyethoxyethanesulfonate and 0.5 g of 5% aqueous solution of p-octylphenoxy polyoxyethylene ether (degree of polymerization: 10) were fed into a 700 ml pot mill. 5.0 g of dye ExF-2 and 500 ml of zirconium oxide beads (diameter: 1 mm) were added thereto, and the mixture was milled with a BO type vibration ball mill (a product of Chuo Koki) for 2 hours to obtain a dispersion. Then the dispersion was taken out and added to 8 g of 12.5% aqueous gelatin solution. The beads were removed by filtration to obtain a dispersion of the dye in gelatin. The average grain diameter of the fine dye grains was 0.44 μm.

A solid dispersion of each of ExF-3, ExF-4 and ExF-6 was obtained in the same manner as that described above. The average grain diameters of the fine dye grains were 0.24 μm, 0.45 μm and 0.52 μm, respectively. ExF-5 was dispersed by a microprecipitation dispersion method described in Example 1 in European Patent Application Kokai (EP) No. 0,549,489 A. The average grain diameter was 0.06 μm.

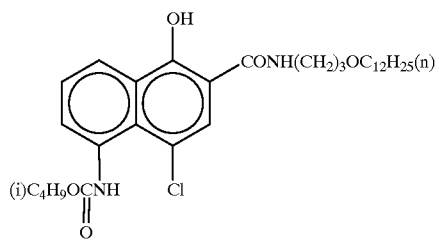

ExC-1

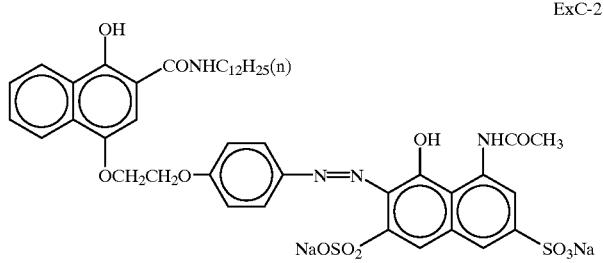

ExC-2

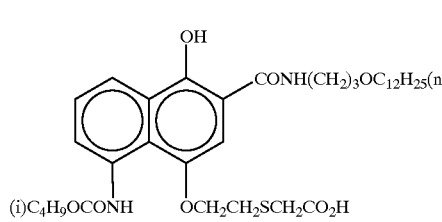

ExC-3

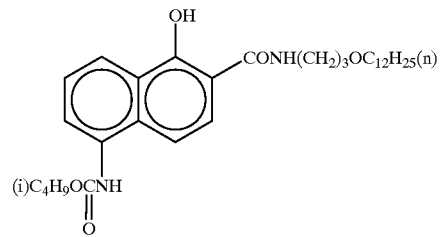

ExC-4

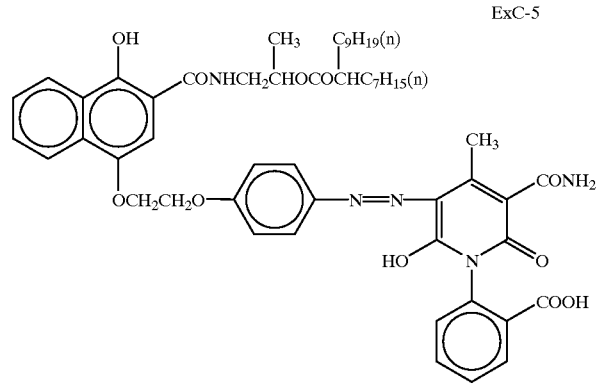

ExC-5

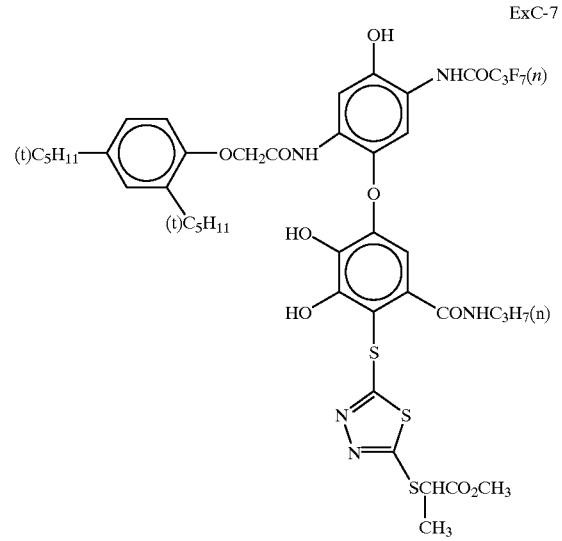

ExC-7

ExC-8
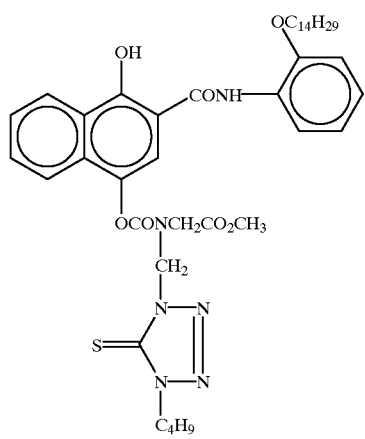
ExM-1
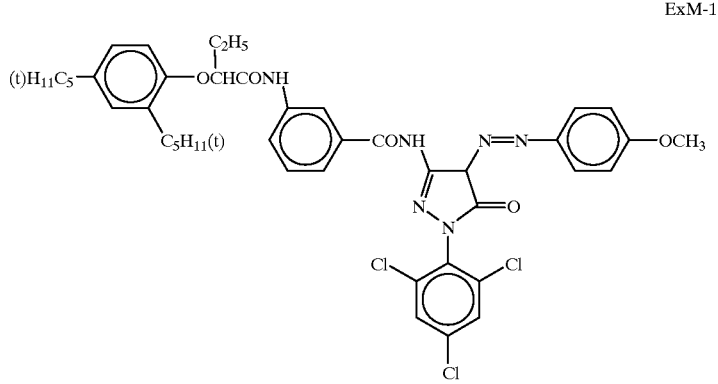
ExM-2
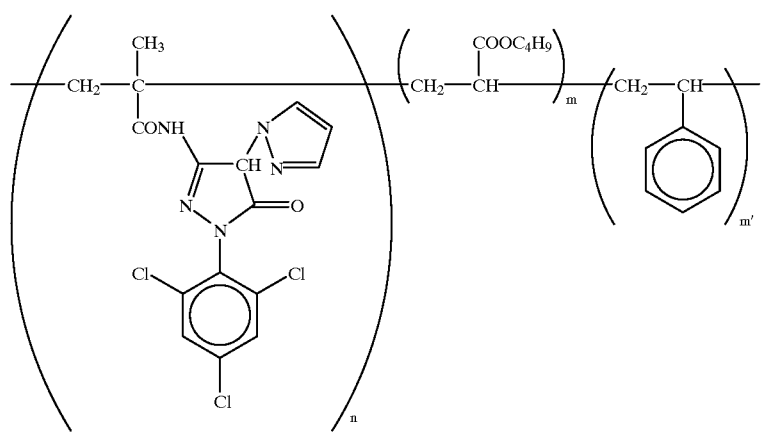
n = 50
m = 25
m' = 25
mol. wt. about 20,000
ExM-3
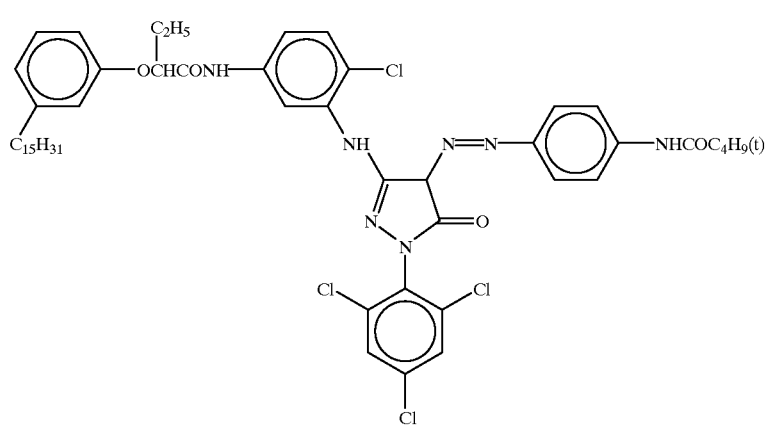

ExM-4
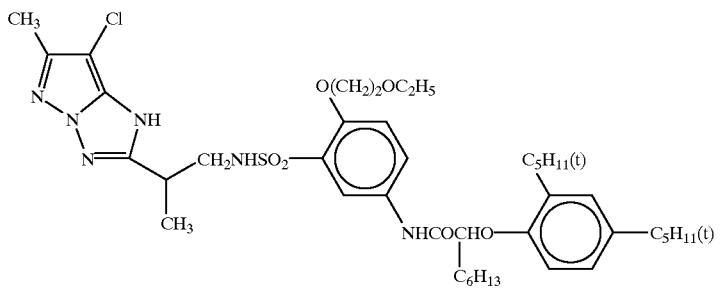
ExM-5
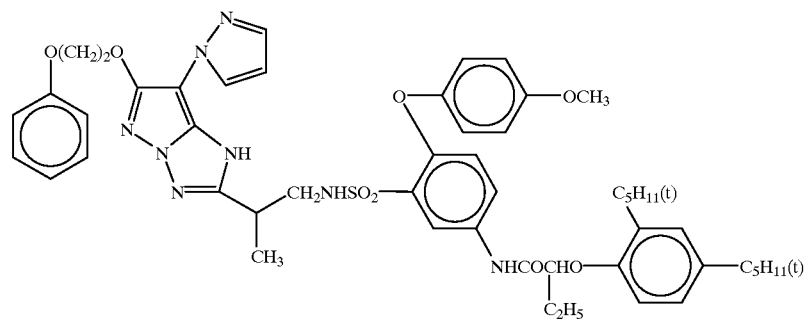
ExY-1
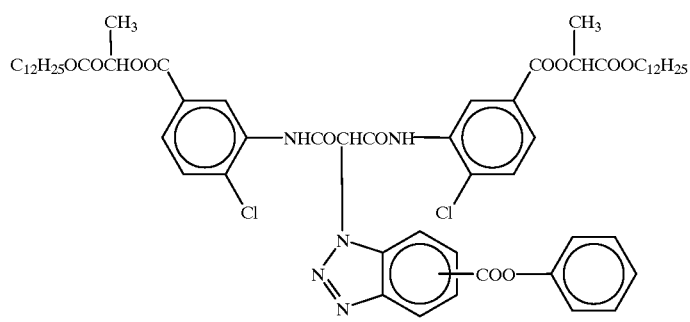
ExY-2
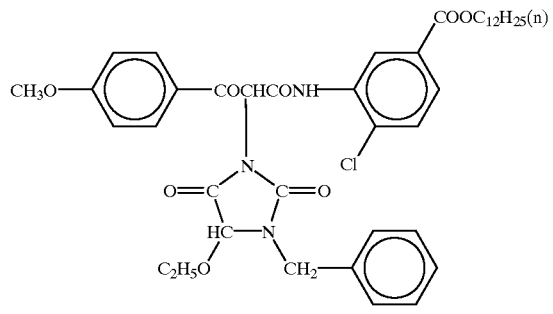
ExY-3
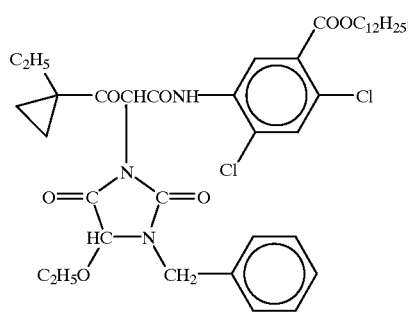

ExY-4
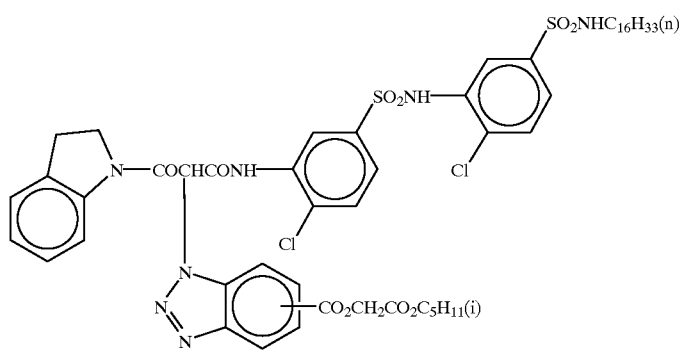
ExY-5
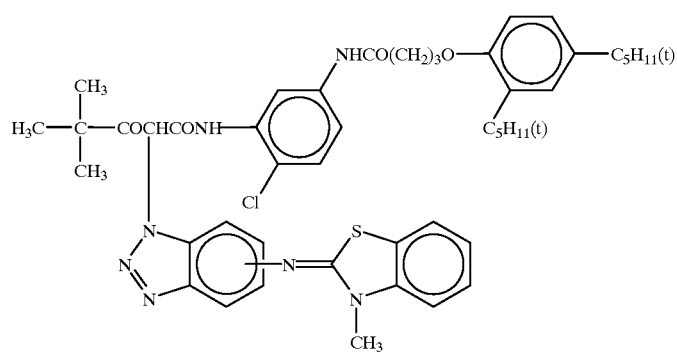
ExY-6
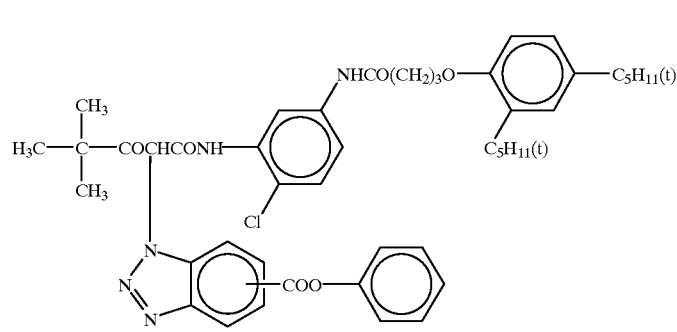
ExF-1
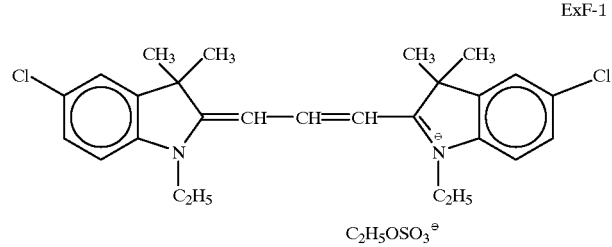
Cpd-1
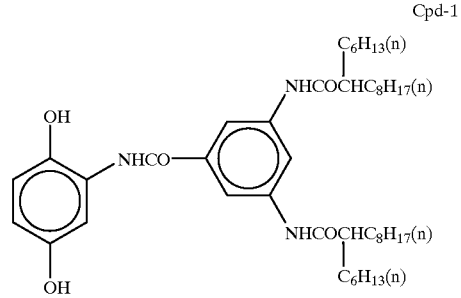
Cpd-2
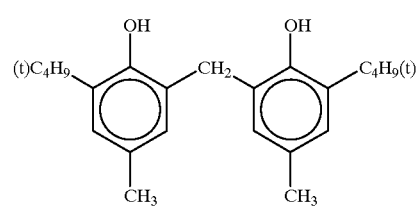
Cpd-3
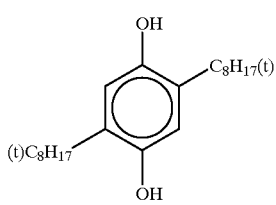

-continued
UV-1
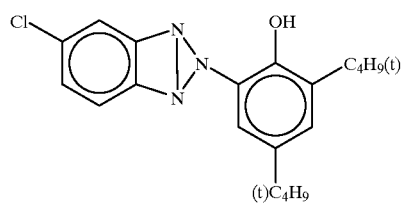
UV-2
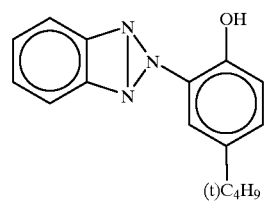
UV-3
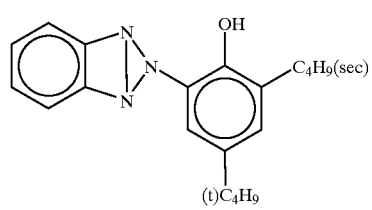
UV-4
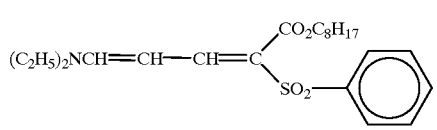
HBS-1
Tricresyl phosphate
HBS-2
Di-n-butyl phthalate
HBS-3
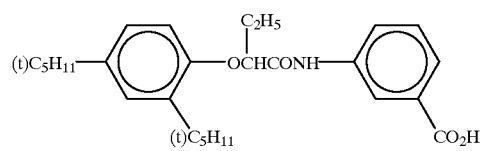
ExS-1
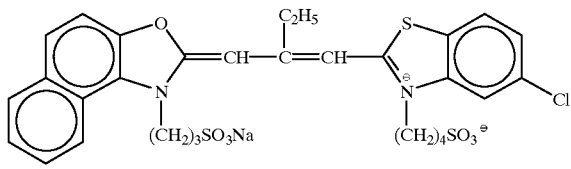
ExS-2
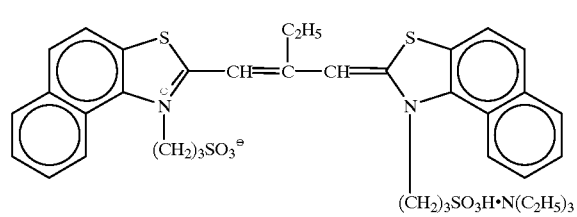
ExS-3
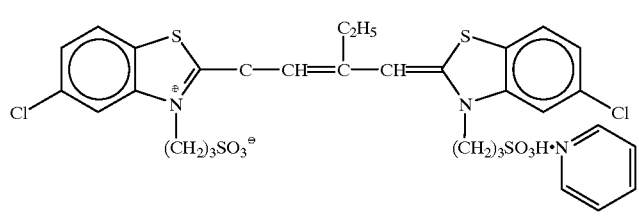
ExS-4
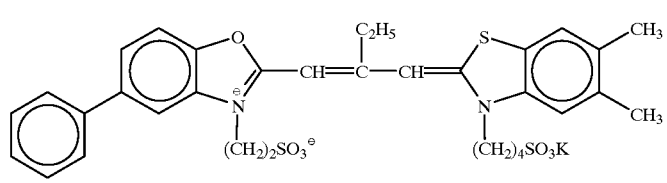
ExS-5
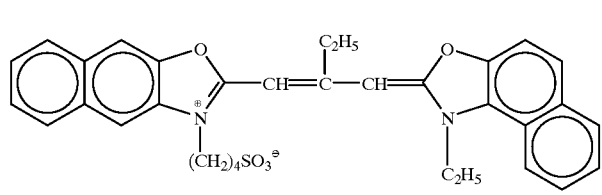

-continued

ExS-6

[Structure: bis-benzoxazole cyanine dye with phenyl and Cl substituents, N-(CH$_2$)$_2$CHCH$_3$-SO$_3^\ominus$ and N-(CH$_2$)$_2$CHCH$_3$-SO$_3$H·N(C$_2$H$_5$)$_3$ side chains, with C$_2$H$_5$ on central methine]

ExS-7

[Structure: bis-benzothiazole cyanine dye with Cl substituents, N-(CH$_2$)$_2$CHCH$_3$-SO$_3^\ominus$ and N-(CH$_2$)$_2$CHCH$_3$-SO$_3$H·N(C$_2$H$_5$)$_3$ side chains]

S-1

[Structure: glycoluril derivative with N-CH$_3$]

H-1

CH$_2$=CH—SO$_2$—CH$_2$—CONH—CH$_2$
CH$_2$=CH—SO$_2$—CH$_2$—CONH—CH$_2$

B-1

$-(CH_2-C(CH_3)(COOH))_x-(CH_2-C(CH_3)(COOCH_3))_y-$ x/y = 10/90

B-2

$-(CH_2-C(CH_3)(COOH))_x-(CH_2-C(CH_3)(COOCH_3))_y-$ x/y = 40/60

B-3

(CH$_3$)$_3$SiO—(Si(CH$_3$)(CH$_2$CH(CH$_3$)C$_6$H$_5$)—O)$_{29}$—(Si(CH$_3$)$_2$—O)$_{46}$—Si(CH$_3$)$_3$

B-4

$-(CH_2-CH(C_6H_4SO_3Na))_n-$

W-1

C$_8$F$_{17}$SO$_2$NHCH$_2$CH$_2$CH$_2$OCH$_2$CH$_2$N$^\oplus$(CH$_3$)$_3$

CH$_3$—C$_6$H$_4$—SO$_3^\ominus$

W-2

C$_8$H$_{17}$—C$_6$H$_4$—(OCH$_2$CH$_2$)$_n$—SO$_3$Na n = 2 ~ 4

W-3

[Naphthalene with C$_4$H$_9$(n) groups and NaO$_3$S substituent]

F-1

HS—[1,3,4-thiadiazole]—SCH$_3$

F-2

[1-(4-carboxyphenyl)-5-mercaptotetrazole, COONa]

F-3

[1-(3-sulfonatophenyl)-5-mercaptotetrazole, SO$_3$Na]

-continued
F-4
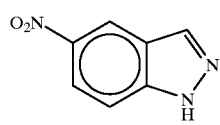
F-5
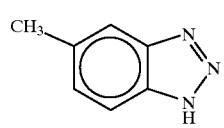
F-6
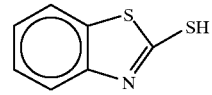
F-7
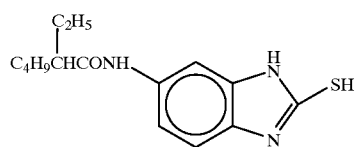
F-8
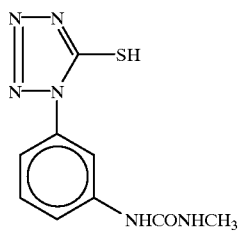
F-9
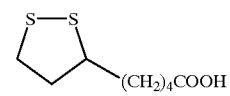
F-10
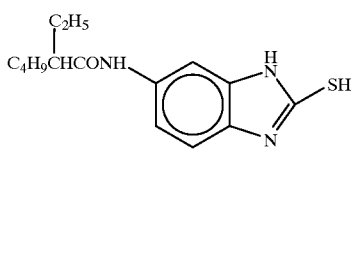
F-11
F-12
F-13
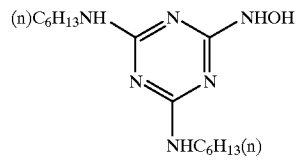
F-14
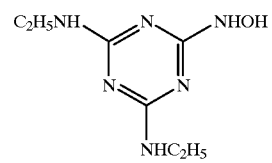
F-15
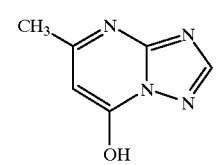
F-16
F-17
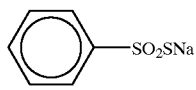
B-5
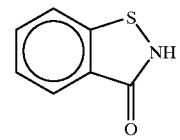
x/y = 70/30
B-6
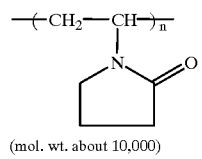
(mol. wt. about 10,000)
ExC-6
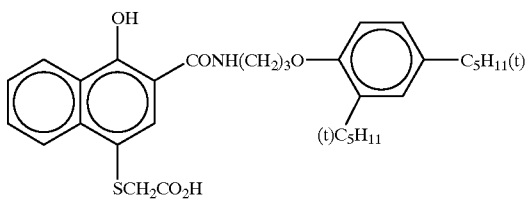
ExF-3
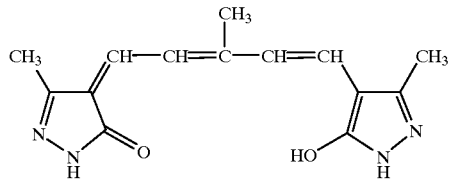
ExF-6
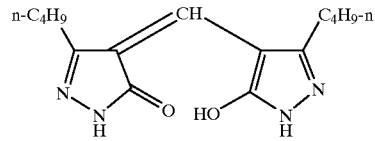

-continued
ExF-7

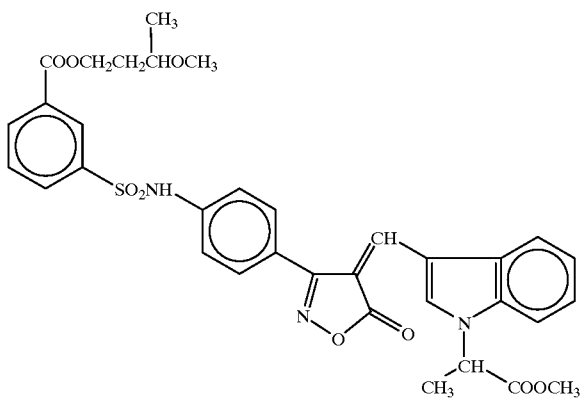

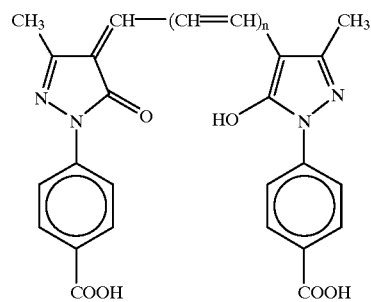

ExF-2 (n = 2)
ExF-4 (n = 1)
ExF-5 (n = 0)

After exposing the above-described color photographic photosensitive material, it was processed by the following method with Nega processor FP-350 (a product of Fuji Photo Film Co., Ltd.) until the total quantity of the replenisher had become three times as much as the capacity of the tank.

| (Proceccing method) (Step) | (Process) time) | (Process temp.) | (Amount of replenisher)* |
|---|---|---|---|
| Color development | 3 min 30 sec | 40° C. | 45 ml |
| Bleaching | 1 min 00 sec | 38° C. | 20 ml |
| | | | The total amount of overflow of bleaching solution flew into the bleach-fixing tank. |
| Bleach-fixing | 3 min 15 sec | 38° C. | 30 ml |
| Washing with water (1) | 40 sec | 35° C. | Countercurrent pipe system from (2) into (1) |
| Washing with water (2) | 1 min 00 sec | 35° C. | 30 ml |
| Stabilization | 40 sec | 38° C. | 20 ml |
| Drying | 1 min 15 sec | 55° C. | |

*The quantity of the replenisher was given per 35 mm width × 1.1 m length (24 Ex. × 1)

The composition of each of the processing liquids was as follows:

| (Color developer) | Mother liquor (g) | Replenisher (g) |
|---|---|---|
| Diethylenetriaminepentaacetic acid | 1.0 | 1.1 |
| 1-hydroxyethylidene-1,1-diphosphonic acid | 2.0 | 2.0 |
| Sodium sulfite | 4.0 | 4.4 |
| Potassium carbonate | 30.0 | 37.0 |
| Potassium bromide | 1.4 | 3.3 |
| Potassium iodide | 1.5 mg | — |
| Hydroxylamine sulfate | 2.4 | 2.8 |
| 4-[N-ethyl-N-(β-hydroxyethyl)amino]-2-methylaniline (P-5) sulfate | 4.5 | 5.5 |
| Water | ad 1.0 l | 1.0 l |
| pH (with potassium hydroxide and sulfuric acid) | 10.05 | 10.10 |

| (Bleaching bath) (common to mother liquor and replenisher) | (unit: g) |
|---|---|
| Ferric ammonium ethylenediaminetetraacetate dihydrate | 120.0 |
| Disodium ethylenediaminetetraacetate | 10.0 |
| Ammonium bromide | 100.0 |
| Ammonium nitrate | 10.0 |
| Bleaching accelerator | 0.005 mol |

-continued

| | |
|---|---|
| $(CH_3)_2N-CH_2-CH_2-S-S-CH_2-CH_2-N(CH_3)_2$.2HCl | |
| Ammonia water (27%) | 15.0 ml |
| Water | ad 1.0 l |
| pH (with ammonia water and nitric acid) | 6.3 |

| (Bleach-fixing bath) | Mother liquor (g) | Replenisher (g) |
|---|---|---|
| Ferric ammonium ethylenediaminetetraacetate dihydrate | 50.0 | — |
| Disodium ethylenediaminetetraacetate | 5.0 | 2.0 |
| Sodium sulfite | 12.0 | 20.0 |
| Aqueous ammonium thiosulfate (700 g/l) | 240.0 ml | 400.0 ml |
| Ammonia water (27%) | 6.0 ml | — |
| Water | ad 1.0 l | ad 1.0 l |
| pH (with ammonia water and acetic acid) | 7.2 | 7.3 |

(Washing water) (common to mother liquor and replenisher)

Tap water was passed through a mixed-bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water. The pH of the water was in the range of 6.5 to 7.5.

| (Stabilizer) (common to the mother liquid and tank liquid) | (unit: g) |
|---|---|
| Sodium p-toluenesulfinate | 0.03 |
| Polyoxyethylene-p-mononylphenyl ether (average degree of polymerization: 10) | 0.2 |
| Disodium ethylenediaminetetraacetate | 0.05 |
| 1,2,4-Triazole | 1.3 |
| 1,4-Bis(1,2,4-triazol-1-ylmethyl)piperazine | 0.75 |
| Water | ad 1 l |
| pH | 8.5 |

The process in which the running processing solution was thus obtained will be referred to as "process 151". Then the same color developer as that described above was prepared except that the color developing agent P-5 contained therein was replaced with the equimolar amount of a comparative color developing agent or the color developing agent of the present invention given in Table 101, and the continuous process was conducted in the same manner as that described above to obtain running processing solutions (processes 152 to 173).

The rapidness of the process was evaluated as follows: after wedge-exposure of the sample 101, it was processed with each of the running processing solutions (processes 152 to 173) while the color development time was changed stepwise from 1 minute to 3 minutes at intervals of 10 seconds. The optical density of the yellow image of each of the resultant samples was determined. The obtained results were compared with the optical density of a yellow image obtained by the color development with the color developing agent P-5 (or, in other words, by process 151) for 3 minutes and 30 seconds. The color development time necessitated for yielding a density of at least 1.8 with an exposure necessitated for yielding an optical density of 1.8 is given in Table 101. The fog density of the yellow image of the sample obtained after the color development time was given in terms of a difference from the fog density of the yellow image of the above-described sample (sample obtained by the color development by the process 151 for 3 minutes and 30 seconds). The results are summarized in Table 101.

Comparative color developing agent:

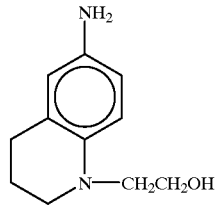

Compound I-(1) described in J. P. KOKAI Hei 4-45, 440    [described also in U.S. Pat. No. 2,196,739]

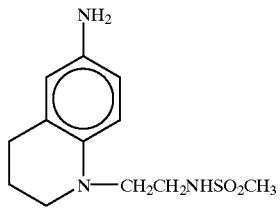

Compound I-(2) described in J. P. KOKAI Hei 4-45, 440    [described also in U.S. Pat. No. 2,566,259]

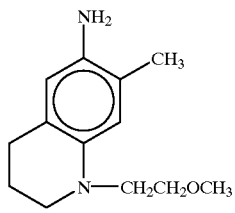

Compound I-(5) described in J. P. KOKAI Hei 4-45, 440

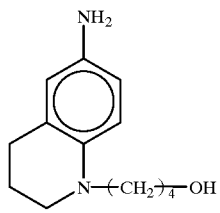

Compound I-(9) described in J. P. KOKAI Hei 4-45, 440

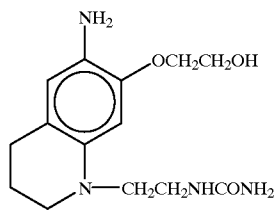

Compound I-(10) described in J. P. KOKAI Hei 4-45, 440

-continued

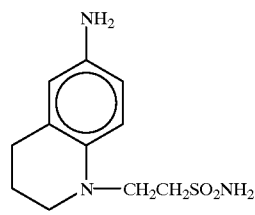

Compound I-(16) described in J. P. KOKAI Hei 4-45, 440

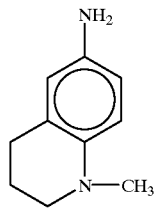

Compound (US-3) described in U.S. Pat. No. 2,196,739

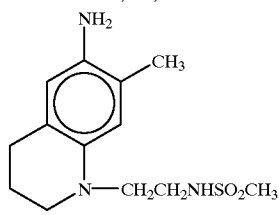

Compound (US-4) described in U.S. Pat. No. 2,566,259

TABLE 101

| Process | Color developing agent | $R_3$ | Process time | Fog dencity (difference) | Remarks |
|---|---|---|---|---|---|
| 152 | I-(1) | H | 2 min. 30 sec. | 0.82 | Comp. Ex. |
| 153 | D-33 | H | 2 min. 30 sec. | 0.01 | Present invention |
| 154 | I-(2) | H | 2 min. 30 sec. | 0.79 | Comp. Ex. |
| 155 | D-4 | H | 2 min. 30 sec. | 0.01 | Present invention |
| 156 | I-(5) | $CH_3$ | 2 min. 10 sec. | 0.96 | Comp. Ex. |
| 157 | D-17 | $CH_3$ | 2 min. 10 sec. | 0.07 | Present invention |
| 158 | I-(9) | H | 2 min. 20 sec. | 0.80 | Comp. Ex. |
| 159 | D-34 | H | 2 min. 20 sec. | 0.02 | Present invention |
| 160 | I-(10) | $OCH_2CH_2OH$ | 1 min. 40 sec. | 1.15 | Comp. Ex. |
| 161 | D-26 | $OCH_2CH_2OH$ | 1 min. 40 sec. | 0.15 | Present invention |
| 162 | I-(16) | H | 2 min. 30 sec. | 0.77 | Comp. Ex. |
| 163 | D-35 | H | 2 min. 30 sec. | −0.01 | Present invention |
| 164 | US-3 | H | 2 min. 30 sec. | 0.88 | Comp. Ex. |
| 165 | D-25 | H | 2 min. 20 sec. | 0.12 | Present invention |
| 166 | US-4 | $CH_3$ | 2 min. 10 sec. | 0.99 | Comp. Ex. |
| 167 | D-36 | $CH_3$ | 2 min. 10 sec. | 0.01 | Present invention |
| 168 | D-2 | $CH_3$ | 2 min. | −0.02 | Present invention |
| 169 | D-11 | $CH_3$ | 2 min. | −0.01 | Present invention |
| 170 | D-18 | $CH_3$ | 2 min. | −0.01 | Present invention |
| 171 | D-7 | $OCHCH_2OH$ \| $CH_3$ | 1 min. 50 sec. | 0.13 | Present invention |
| 172 | D-38 | $CH_3$ | 2 min. 10 sec. | −0.00 | Present invention |
| 173 | D-39 | $CH_3$ | 2 min. | −0.01 | Present invention |

It is apparent from Table 101 that the color developing agent of the present invention is capable of attaining the intended density of the yellow image in a development process time far shorter than that of P-5 (process No. 151). However, this effect can be obtained with also a color developing agent described in, for example, J. P. KOKAI No. Hei 4-45,440 given herein for comparison.

It is also apparent that the fog density of the yellow image is very high with the color developing agents in the comparative example. On the contrary, it will be apparent by comparison of the process 152 with process 153, 154 with 155, 156 with 157, 158 with 159, 160 with 161, 162 with 163, 164 with 165 or 166 with 167 that the color developing agent of the present invention is capable of controlling the fog density of the yellow image on a low level while keeping the rapidness of the process. This fact proved that the introduction of the two substituents into one carbon atom of the saturated ring of the tetrahydroquinoline derivatives greatly change the properties.

Although the yellow image can be obtained extremely rapidly by selecting the variety of the substituent $R_8$ as in, for example, process 169, the fog density is relatively high in the color developing agent of the present invention. On the contrary, although the rapidness in processes 164 and 167 is slightly lower than that in process 169, the fog density in the former is kept very low. They are preferred color developing agents from the viewpoint of the object of the present invention, i.e. compatibility of rapidness with low fog density.

Thus, the compatibility of rapidness with reduction of the fog density cannot be attained before the development of the color developing agent of the present invention. It is impossible to infer it from the color developing agent used in the comprative example.

EXAMPLE 2

Sample 101 in Example 1 was exposed, and then it was developed with compound (D-18) of the present invention as the color developing agent in the color developer by a method described below. A desired gradation could be obtained in a color development time of as short as 60 seconds. The fog density was low favorably. When compound (D-30) was used in place of compound (D-18), the results similar to those described as above could be obtained.

| Development steps and composition of processing solution: | | |
| --- | --- | --- |
| Step | Temperature | Time |
| Color development | 45° C. | 60 sec |
| Bleach-fixing | 45° C. | 60 sec |
| Washing with water (1) | 40° C. | 15 sec |
| Washing with water (2) | 40° C. | 15 sec |
| Washing with water (3) | 40° C. | 15 sec |
| Stabilization | 40° C. | 15 sec |
| Drying | 80° C. | 30 sec |

[The washing with water was conducted by counter-current method from (3) to (1).]

| Composition of processing liquids: | |
| --- | --- |
| (Color developer) | Mother liquor (g) |
| Diethylenetriaminepentaacetic acid | 4.0 |
| 1-Hydroxyethylidene-1,1-diphosphonic acid | 3.0 |
| Sodium sulfite | 4.0 |
| Potassium carbonate | 50.0 |
| Potassium bromide | 4.0 |
| Potassium iodide | 1.3 mg |
| Hydroxylamine sulfate | 4.0 |
| The above-mentioned developing agent | 18.0 |
| Water | ad 1.0 l |
| pH (adjusted with potassium hydroxide and sulfuric acid) | 10.05 |

| (Bleach-fixing bath) | (unit: mol) |
| --- | --- |
| Chelating agent of formula A | 0.17 |
| Ferric nitrate nonahydrate | 0.15 |
| Ammonium thiosulfate | 1.25 |
| Ammonium sulfite | 0.10 |
| Metacarboxybenzenesulfinic acid | 0.05 |

| -continued | |
| --- | --- |
| Water | ad 1.0 l |
| pH (adjusted with acetic acid and ammonia) | 5.8 |

Formula A

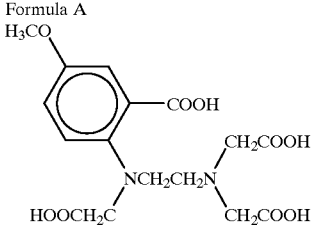

(Washing water)

Tap water was passed through a mixed bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water. pH of the water was in the range of 6.5 to 7.5.

| (Stabilizing bath) | Mother liquor (g) |
| --- | --- |
| 1,2-Benzoisothiazoline-3-on | 0.1 |
| Polyoxyethylene p-monononylphenyl ether (average degree of polymerization: 10) | 0.2 |
| Water | ad 1.0 l |
| pH (adjusted with ammonia water and hydrochloric acid) | 8.50 |

EXAMPLE 3

Sample 101 in Example 1 was exposed, and then it was developed with compound (D-18) of the present invention as the color developing agent in the color developer by a method described below until the total quantity of the replenisher had become three times as much as the capacity of the tank.

| (Processing step) (Step) | (Process time) | (Process temp.) | (Amount of replenisher)* | (Capacity of tank) |
| --- | --- | --- | --- | --- |
| Color development | 1 min 30 sec | 45.0° C. | 200 ml | 2.0 l |
| Bleaching | 30 sec | 45.0° C. | 130 ml | 0.7 l |
| Fixing (1) | 30 sec | 45.0° C. | 100 ml | 0.7 l |
| Fixing (2) | 30 sec | 45.0° C. | 70 ml | 0.7 l |
| Washing with water (1) | 15 sec | 45.0° C. | — | 0.4 l |
| Washing with water (2) | 15 sec | 45.0° C. | — | 0.4 l |
| Washing with water (3) | 15 sec | 45.0° C. | 400 ml | 0.4 l |
| Drying | 20 sec | 80° C. | | |

*The quantity of the replenisher was given per $m^2$ of the photosensitive material.
[The steps ranging from washing with water (3) to fixing (2) were conducted by counter-current multistage cascade method with four tanks.]
[The steps ranging from fixing (2) to fixing (1) were conducted by counter-current multistage cascade method with two tanks.]

The composition of each of the processing liquids was as follows:

| (Color developer) | Mother liquor (g) | Replenisher (g) |
|---|---|---|
| Diethylenetriaminetetraacetic acid | 4.0 | 4.0 |
| Sodium 4,5-dihydroxybenzene-1,3-disulfonate | 0.5 | 0.5 |
| Sodium sulfite | 3.9 | 6.5 |
| Potassium carbonate | 37.5 | 39.0 |
| Potassium bromide | 2.7 | — |
| Potassium iodide | 1.3 mg | — |
| N-methylhydroxylamine hydrochloride | 4.5 | 5.5 |
| The above-inentioned developing agent | 8.0 | 12.0 |
| Water | ad 1.0 l | 1.0 l |
| pH (with potassium hydroxide and sulfuric acid) | 10.05 | 10.25 |

| (Bleaching bath) | Mother liquor (mol) | Replenisher (mol) |
|---|---|---|
| Ferric ammonium 1,3-diaminopropane-tetraacetate monohydrate | 0.33 | 0.50 |
| Ferric nitrate nonahydrate | 0.30 | 4.5 |
| Ammonium bromide | 0.80 | 1.20 |
| Ammonium nitrate | 0.20 | 0.30 |
| Acetic acid | 0.67 | 1.0 |
| Water | ad 1.0 l | 1.0 l |
| pH [with ammonia water] | 4.5 | 4.0 |

| (Fixing bath) (common to mother liquor and replenisher) | (g) |
|---|---|
| Ammonium sulfite | 28 |
| Aqueous ammonium thiosulfate solution (700 g/l) | 280 ml |
| Imidazole | 15 |
| Ethylenediaminetetraacetic acid | 15 |
| Water | ad 1.0 l |
| pH (with ammonia water and acetic acid) | 5.8 |

(Washing water) (common to mother liquor and replenisher)

Tap water was passed through a mixed bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water. pH of the water was in the range of 6.5 to 7.5.

| (Stabilizer) (common to the mother liquor and replenisher) | (unit: g) |
|---|---|
| 1,2-Benzoisothiazoline-3-on | 0.1 |
| Polyoxyethylene-p-monononylphenyl ether (average degree of polymerization: 10) | 0.2 |
| Water | ad 1 l |
| pH [adjusted with ammonia water and hydrochloric acid] | 8.50 |

The sample 101 was exposed and processed with the running-processing solution. A desired gradation could be attained in a color development time of as short as 1 minute and 30 seconds. The fog density was low favorably. When the compound (D-18) was replaced with the compound (D-30), the similar results could be obtained.

EXAMPLE 4

The same continuous process as that described in Example 1 of J. P. KOKAI No. Hei 5-333501 was conducted by using the sample 101 used therein except that N-ethyl-(β-methanesulfonamidoethyl)-3-methyl-4-aminoaniline 3/2 sulfate monohydrate in the color developer was replaced with the equimolar amount of the compound (D-18) of the present invention to obtain a developing bath in the running equilibrium state. When the sample 101 was exposed and processed with the running-processing solution, a desired density could be obtained in a short color development time. The fog density was low favorably.

EXAMPLE 5

Sample 101 in Example 4 was formed into a roll having a width of 127 mm, which was then subjected to the running test until the total quantity of the replenisher had become twice as much as the capacity of the color development tank.

| Processing step | Temp. | Time | Amount of replenisher* | Capacity of tank (l) |
|---|---|---|---|---|
| Color development | 38.5° C. | 45 sec | 73 ml | 10 |
| Bleach-fixing | 35° C. | 45 sec | 60 ml** | 10 |
| Rinsing (1) | 35° C. | 30 sec | — | 8 |
| Rinsing (2) | 35° C. | 30 sec | — | 8 |
| Rinsing (3) | 35° C. | 30 sec | 360 ml* | 8 |
| Drying | 80° C. | 60 sec | | |

*The quantity of the replenisher was given per $m^2$ of the photosensitive material.
**120 ml, per $m^2$ of the photosensitive material, of the solution was replenished from the rinse (1) in addition to the above-mentioned 60 ml of the replenisher. [The rinsing was conducted by counter-current method from (3) to (1) with three tanks.]

The composition of each of the processing liquors was as follows:

| (Color developer) | Mother liquor | Replenisher |
|---|---|---|
| Water | 800 ml | 800 ml |
| Ethylenediaminetetraacetic acid | 3.0 g | 3.0 g |
| Disodium 4,5-dihydroxybenzene-1,3-disulfonate | 0.5 g | 0.5 g |
| Triethanolamine | 12.0 g | 12.0 g |
| Potassium chloride | 6.5 g | — |
| Potassium bromide | 0.33 g | — |
| Potassium carbonate | 27.0 g | 27.0 g |
| Fluorescent brightener (WHITEX 4; a product of Sumitomo Chemical Co., Ltd.) | 1.0 g | 3.0 g |
| Sodium sulfite | 0.1 g | 0.1 g |
| Disodium N,N-bis(sulfonatoethyl)hydroxylamine | 5.0 g | 10.0 g |
| Sodium triisopropylnaphthalene(β)sulfonate | 0.1 g | 0.1 g |
| Compound (D-18) | 11.5 mmol | 26.3 mmol |
| 1,5-naphthalenedisulfonate | | |
| Water | ad 1000 ml | 1000 ml |
| pH (25° C./with potassium hydroxide and sulfuric acid) | 10.00 | 11.00 |

| (Bleach-fixing bath) | Mother liquor | Replenisher |
|---|---|---|
| Water | 600 ml | 150 ml |
| Ammonium thiosulfate (750 g/l) | 93 ml | 230 ml |
| Ammonium sulfite | 40 | 100 g |
| Ferric ammonium ethylenediamine-tetraacetate | 55 | 135 g |
| Ethylenediaminetetraacetic acid | 5 | 12.5 g |
| Nitric acid (67%) | 30 | 65 g |
| Water | ad 1000 ml | 1000 ml |
| pH [25° C./adjusted with acetic acid and ammonia water] | 5.8 | 5.6 |

| -continued | |
|---|---|
| (Rinsing water) (common to mother liquor and replenisher) | |
| Sodium isocyanurate chloride | 0.02 g |
| Deionized water (conductivity: 5 µs/cm or below) | 1000 ml |
| pH | 6.5 |

The sample 101 was exposed and processed with the continuous processing solutions to obtain an intended density in a short color development time. The fog density was low favorably.

EXAMPLE 6

The same continuous process as that described in Example 1 of Japanese Patent Application No. Hei 5-67352 was conducted by using the sample 115b (in the preparation of this sample, the coating solution was used after leaving it at 40° C. for 8 hours) used therein except that N-ethyl-(β-methanesulfonamidoethyl)-3-methyl-4-aminoaniline 3/2 sulfate monohydrate in the color developer was replaced with the equimolar amount of the compound (D-18) of the present invention to obtain a developing bath in the running equilibrium state. When the sample 115b was exposed and processed with the running-processing solution, an intended density could be obtained in a short color development time. The fog density was low favorably. Compounds (D-39) or (D-42) was used in place of compounds (D-18) and therefore, the same results were obtained.

It will be apparent from Examples that the color developing agent of the present invention us suitable for the rapid process and that an image of a low fog density can be obtained with it.

What is claimed is:

1. A color developing agent which is represented by the following formula (II):

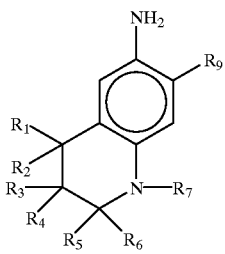

wherein $R_1$, $R_2$, $R_3$, $R_4$, $R_5$ and $R_6$ each represents a hydrogen atom or an alkyl group having 1 to 3 carbon atoms, $R_7$ is an alkyl group having 1 to 6 carbon atoms, and $R_9$ is an alkyl group having 1 to 6 carbon atoms, provided that in at least one of the groups of $R_1$ and $R_2$, $R_3$ and $R_4$, and $R_5$ and $R_6$, both of the R groups are alkyl groups, and at least one of $R_1$ to $R_7$ is an alkyl group substituted with a water-soluble group.

2. The color developing agent of claim 1 wherein $R_9$ is a methyl group.

3. The color developing agent of claim 1 wherein at least one of $R_1$ to $R_7$ and $R_9$ is an alkyl group substituted with a water-soluble group.

4. The color developing agent of claim 1 wherein the water-soluble group is a hydroxyl, carboxyl, ureido or sulfoamido group.

5. The color developing agent of claim 3 wherein the water-soluble group is a hydroxyl, carboxyl, ureido or sulfoamido group.

* * * * *